US008827961B2

(12) United States Patent
Emmott et al.

(10) Patent No.: US 8,827,961 B2
(45) Date of Patent: Sep. 9, 2014

(54) SAFETY NEEDLE

(75) Inventors: Douglas Arthur Emmott, Ipswich (GB); Paul H. Norton, Trumbauersville, PA (US); Anthony Licence, Woodbridge (GB); Terence Edward Weston, Swannington (GB); Anthony L. Eaton, Watsontown, PA (US)

(73) Assignee: West Pharmaceutical Services, Inc., Exton, PA (US)

( * ) Notice: Subject to any disclaimer, the term of this patent is extended or adjusted under 35 U.S.C. 154(b) by 242 days.

(21) Appl. No.: 12/470,220

(22) Filed: May 21, 2009

(65) Prior Publication Data
US 2009/0227956 A1 Sep. 10, 2009

Related U.S. Application Data

(63) Continuation-in-part of application No. 11/815,475, filed as application No. PCT/GB2005/000357 on Feb. 3, 2005, now Pat. No. 8,235,950.

(51) Int. Cl.
*A61M 5/32* (2006.01)
*A61M 5/00* (2006.01)
*A61M 5/50* (2006.01)

(52) U.S. Cl.
CPC ............. *A61M 5/002* (2013.01); *A61M 5/5086* (2013.01); *A61M 2005/3267* (2013.01); *A61M 2005/3268* (2013.01); *A61M 5/3272* (2013.01); *A61M 5/326* (2013.01); *A61M 2005/3247* (2013.01)
USPC ............ 604/198; 604/263; 206/365; 206/363

(58) Field of Classification Search
CPC . A61M 5/002; A61M 5/3202; A61M 5/3213; A61M 5/3204; A61M 5/3257; A61M 2005/3247; A61M 25/0618; A61M 25/0631; A61J 2001/2006; A61J 2001/2013; A61J 2001/201; Y10S 128/919
USPC ......... 604/110, 111, 192, 193, 197, 198, 199, 604/263; 206/363, 364, 365, 367
See application file for complete search history.

(56) References Cited

U.S. PATENT DOCUMENTS 1,845,036 A    2/1932  Busher
2,677,373 A *  5/1954  Barradas ....................... 604/192
(Continued)

FOREIGN PATENT DOCUMENTS

CN    1777453 A    5/2006
EP    0467173 A1   1/1992
(Continued)

OTHER PUBLICATIONS

Partial European Search Report for the related European Application No. 09175295.6 dated Apr. 9, 2010.
(Continued)

*Primary Examiner* — Kami A Bosworth
(74) *Attorney, Agent, or Firm* — Panitch Schwarze Belisario & Nadel LLP

(57) ABSTRACT

A safety needle for automatically covering a tip of a needle following removal of the needle from a patient is provided. The safety needle includes an injection device and a packing sleeve. The injection device has an initial position and an intermediate position. The packing sleeve has a generally hollow body surrounding at least a portion of the injection device in the initial position and the intermediate position. The hollow body includes at least one track having an activation leg and a releasing leg. The at least one track is configured to slidingly engage with at least one member of the injection device to move the injection device to the intermediate position. The packing sleeve is removable from the injection device only when the injection device is in the intermediate position.

13 Claims, 19 Drawing Sheets

(56) References Cited

U.S. PATENT DOCUMENTS

| | | | |
|---|---|---|---|
| 3,114,455 | A | 12/1963 | Claisse et al. |
| 3,134,380 | A | 5/1964 | Armao |
| 3,677,245 | A | 7/1972 | Welch |
| 4,553,541 | A | 11/1985 | Burns |
| 4,735,203 | A | 4/1988 | Ryder et al. |
| 4,795,432 | A | 1/1989 | Karczmer |
| 4,813,940 | A | 3/1989 | Parry |
| 4,850,996 | A | 7/1989 | Cree |
| 4,911,693 | A | 3/1990 | Paris |
| 4,927,019 | A | 5/1990 | Smedley et al. |
| 5,015,240 | A | 5/1991 | Charmasson et al. |
| 5,104,384 | A | 4/1992 | Parry |
| 5,219,339 | A | 6/1993 | Saito |
| 5,242,401 | A | 9/1993 | Colsky |
| 5,273,539 | A | 12/1993 | Chen |
| 5,312,366 | A | 5/1994 | Vailancourt |
| 5,336,197 | A | 8/1994 | Kuracina et al. |
| 5,385,561 | A | 1/1995 | Cerny |
| 5,421,347 | A | 6/1995 | Enstrom |
| 5,549,568 | A | 8/1996 | Shields |
| 5,601,535 | A | 2/1997 | Byrne et al. |
| 5,658,256 | A | 8/1997 | Shields |
| 5,669,888 | A | 9/1997 | Trapp |
| 5,755,696 | A * | 5/1998 | Caizza ............ 604/164.11 |
| 5,891,103 | A | 4/1999 | Burns |
| 5,910,130 | A | 6/1999 | Caizza et al. |
| 5,944,699 | A | 8/1999 | Barrelle et al. |
| 5,971,966 | A | 10/1999 | Lav |
| 6,203,529 | B1 | 3/2001 | Gabriel et al. |
| 6,210,374 | B1 | 4/2001 | Malencheck |
| 6,261,264 | B1 | 7/2001 | Tamaro |
| 6,331,174 | B1 | 12/2001 | Spallek et al. |
| 6,398,762 | B1 | 6/2002 | Otto et al. |
| 6,511,460 | B1 | 1/2003 | Arnissolle |
| 6,537,259 | B1 | 3/2003 | Niermann |
| 6,685,676 | B2 | 2/2004 | Jansen et al. |
| 7,041,086 | B2 | 5/2006 | Yang |
| 7,182,734 | B2 | 2/2007 | Saulenas et al. |
| 7,223,258 | B2 | 5/2007 | Crawford |
| 7,713,280 | B2 | 5/2010 | Marshall et al. |
| 2002/0004648 | A1 | 1/2002 | Larsen et al. |
| 2002/0087180 | A1 | 7/2002 | Searle et al. |
| 2003/0014018 | A1 * | 1/2003 | Giambattista et al. ........ 604/198 |
| 2003/0144633 | A1 | 7/2003 | Kirchhofer |
| 2004/0116877 | A1 | 6/2004 | Yang |
| 2004/0210196 | A1 | 10/2004 | Bush, Jr. et al. |
| 2005/0038391 | A1 | 2/2005 | Wittland et al. |
| 2006/0129173 | A1 | 6/2006 | Wilkinson |
| 2006/0167411 | A1 | 7/2006 | Weston et al. |
| 2008/0183140 | A1 | 7/2008 | Paproski et al. |

FOREIGN PATENT DOCUMENTS

| | | | |
|---|---|---|---|
| EP | 0744183 | A2 | 11/1996 |
| EP | 0815884 | A1 | 1/1998 |
| EP | 1252907 | A1 | 10/2002 |
| EP | 1447108 | A1 | 8/2004 |
| EP | 1535640 | A1 | 6/2005 |
| EP | 1558311 | B1 | 8/2005 |
| FR | 2701848 | A1 | 2/1993 |
| JP | 3158171 | A | 7/1991 |
| WO | 91/11212 | A1 | 8/1991 |
| WO | 9400172 | A1 | 1/1994 |
| WO | 9419036 | A1 | 9/1994 |
| WO | 01/76665 | A1 | 10/2001 |
| WO | 01/91837 | A1 | 12/2001 |
| WO | 02/089878 | A1 | 11/2002 |
| WO | 02/100467 | A2 | 12/2002 |
| WO | 03/066141 | A1 | 8/2003 |
| WO | 04/000397 | A1 | 12/2003 |
| WO | 2004/071560 | A1 | 8/2004 |
| WO | 2004069302 | A2 | 8/2004 |
| WO | 2006/090118 | A1 | 8/2006 |
| WO | 2008067467 | A2 | 6/2008 |

OTHER PUBLICATIONS

Chinese Office Action for the related Chinese Application No. 200680006138.6 dated Apr. 15, 2010.
International Preliminary Report on Patentability for the related International Application No. PCT/US2008/077352 dated Apr. 13, 2010.
The Third Chinese Office Action for related Chinese Patent Application No. 200480006925.1; dated Jul. 10, 2009; English translation only (3 pages).
Notification of Transmittal of the International Search Report and the Written Opinion of the International Searching Authority, or the Declaration, Mailed Nov. 19, 2007.
United States Patent and Trademark Office Action mailed Oct. 1, 2008.
Office Action issued Jul. 30, 2010 in Chinese Application No. 20068006138.6.
Office Action for the related U.S. Appl. No. 11/815,475 issued Apr. 9, 2009.
Office Action for the related U.S. Appl. No. 11/815,475 issued Aug. 21, 2009.
International Search Report and Written Opinion for the related International Patent Application No. PCT/GB2005/000357, issued Aug. 26, 2005.
Search Report for the related U.K. Patent Application No. 0621157.7; dated Jan. 25, 2007.
International Search Report for the related International Patent Application No. PCT/GB2004/000516; mailed May 27, 2004.
European Search Report for the related European Patent Application No. 03 25 7489; dated May 25, 2004.
Office Action for the related U.S. Appl. No. 10/545,160 issued Aug. 18, 2009.
Examination Report in the related Australian Patent Application No. 2004212245, dated Nov. 11, 2008.
First Chinese Office Action for the related Chinese Patent Application No. 200480006925.1; dated Dec. 28, 2007; English translation only.
Second Chinese Office Action for the related Chinese Patent Application No. 200480006925.1; dated Feb. 20, 2009; English translation only.
European Search Report for the related European Patent Application No. 03 25 2192, dated May 26, 2003.
Office Action for the related Japanese Patent Application No. 2006-502257 issued Sep. 11, 2009.
Office Action for the related Chinese Patent Application No. 2005800477077 issued Sep. 25, 2009.
Written Opinion for the related International Patent Application No. PCT/GB2004/000516 issued May 27, 2004.
Chinese Office Action for the related Chinese Patent Application No. 200680006138.6; dated Jun. 5, 2009; 8 pages (including English translation).
Office Action for the related U.S. Appl. No. 11/815,475 issued Jan. 4, 2010.
International Search Report and Written Opinion for the related International Patent Application No. PCT/GB2006/000528 issued May 22, 2006.
Office Action for the related U.S. Appl. No. 11/817,075 issued Dec. 21, 2009.
Chinese Office Action for the related Chinese Patent Application No. 200680006138.6 dated Dec. 11, 2009; English translation only.
Japanese Office Action for the related Japanese Application No. 2006-502257 mailed Jan. 15, 2010.
Office Action for the related U.S. Appl. No. 10/545,160 dated Mar. 3, 2010.
Office Action for the related U.S. Appl. No. 11/817,075 dated Aug. 27, 2008.
Office Action for the related U.S. Appl. No. 11/817,075 dated Feb. 20, 2009.
Office Action for the related U.S. Appl. No. 11/817,075 dated Jul. 28, 2009.
International Search Report and Written Opinion for the related International Application No. PCT/US2008/077352 mailed Jan. 30, 2009.

(56) References Cited

OTHER PUBLICATIONS

European Search Report issued on Oct. 4, 2010 in European Patent Application No. EP 09 17 5295.
Office Action Issued Sep. 7, 2010 in Japanese Patent Application No. 2007-553675.
Office Action issued Dec. 23, 2011 in U.S. Appl. No. 12/276,679.
Office Action issued Jan. 5, 2012 in U.S. Appl. No. 12/680,811.
Office Action issued Jul. 29, 2011 in U.S. Appl. No. 11/817,075.
Definition of "seal" as found on Merriam-Webster.com, retrieved Jul. 21, 2011.
Office Action Issued Oct. 6, 2011 in U.S. Appl. No. 10/545,160.
Witness statement of T. E. Weston (inventor), Aug. 27, 2010.
Second witness statement of T. E. Weston (inventor), Mar. 24, 2011.
Third witness statement of T. E. Weston (inventor), Jan. 5, 2012.
Witness statement of John Davison, May 3, 2011.
Statement from claimant in UK revocation proceeding regarding EP Patent No. 1558311, Jul. 15, 2010.
Defendant's counter-statement in UK revocation proceeding regarding EP Patent No. 1558311, Aug. 31, 2010.
Defendant's supplementary counter-statement in UK revocation proceeding regarding EP Patent No. 1558311, Mar. 25, 2011.
Written Preliminary Evaluation in UK revocation proceeding regarding EP Patent No. 1558311, Nov. 10, 2011.
Witness statement of Barry Peter Liversidge on behalf of tip-top.com Ltd. in UK revocation proceeding regarding EP Patent No. 1558311, Jan. 19, 2012.
Defendant's further counter-statement in UK revocation proceeding regarding EP Patent No. 1558311, Jan. 17, 2012.
Defendant's consolidated counter-statement in UK revocation proceeding regarding EP Patent No. 1558311, Mar. 9, 2012.
Office Action Issued Apr. 29, 2011 in U.S. Appl. No. 12/276,679.
Office Action issued Apr. 26, 2011 in JP Application No. 2007-556647.
Office Action issued Jun. 17, 2011 in U.S. Appl. No. 12/680,811.
Office Action issued Aug. 1, 2012 in U.S. Appl. No. 12/680,811.
Office Action issued Dec. 5, 2012 in U.S. Appl. No. 12/276,679.
Office Action issued Sep. 23, 2011 in CN Application No. 200880110889.1.
Office Action issued Nov. 18, 2011 in U.S. Appl. No. 11/817,075.
Office Action issued Jan. 22, 2014 in U.S. Appl. No. 11/817,075 by Weston.
Office Action issued May 2, 2014 in IN Application No. 6141/DELNP/2007.
Office Action issued May 9, 2014 in BR Application No. PI0407376-2.

* cited by examiner

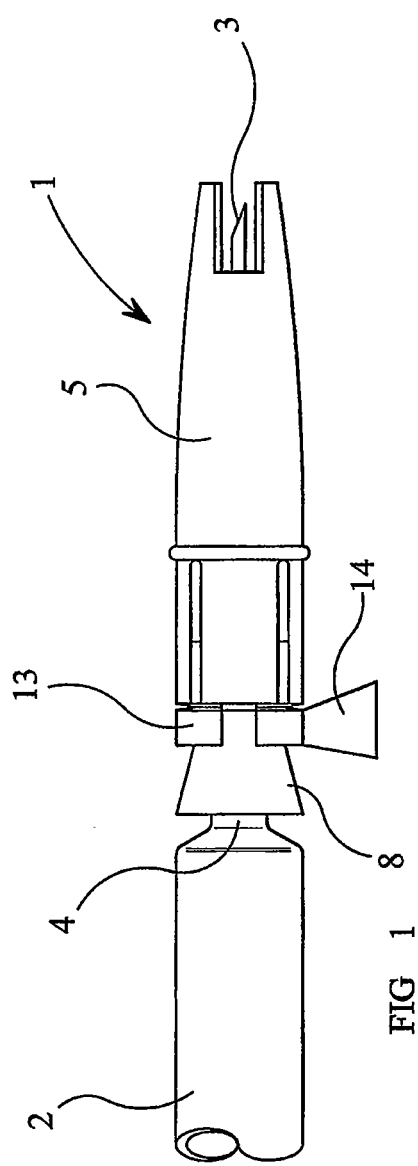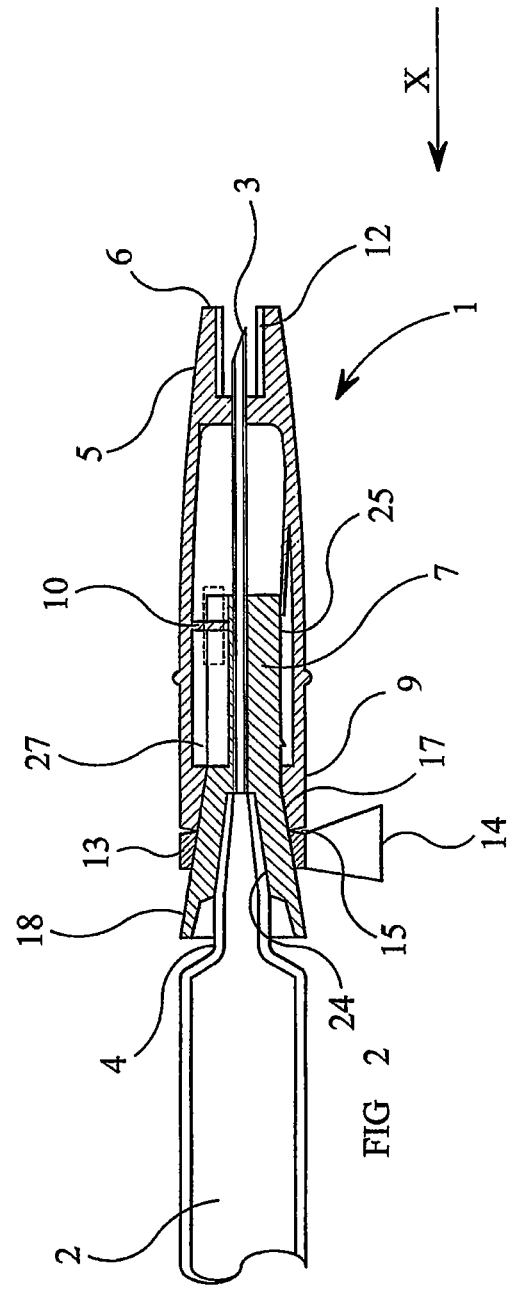

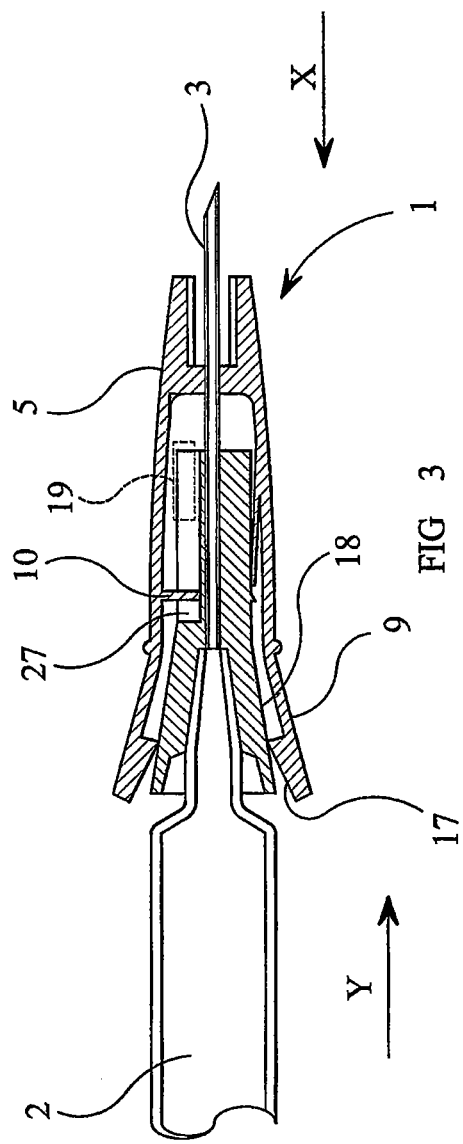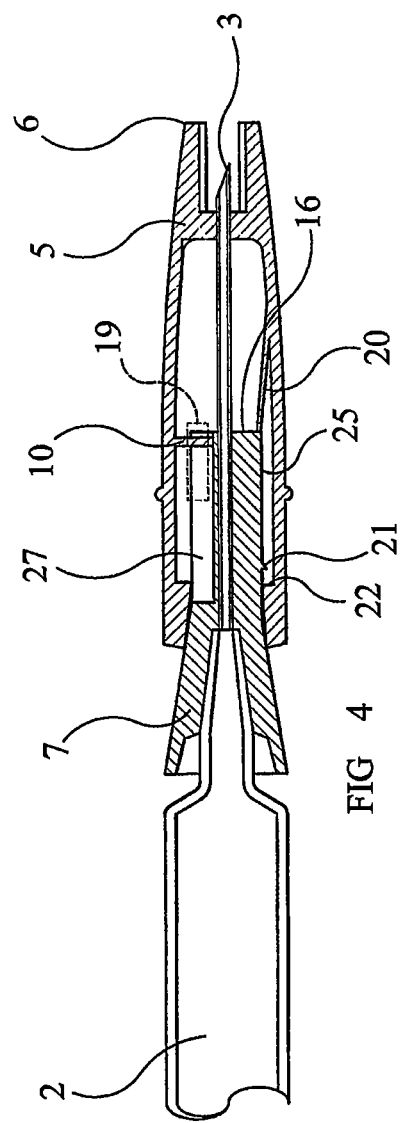

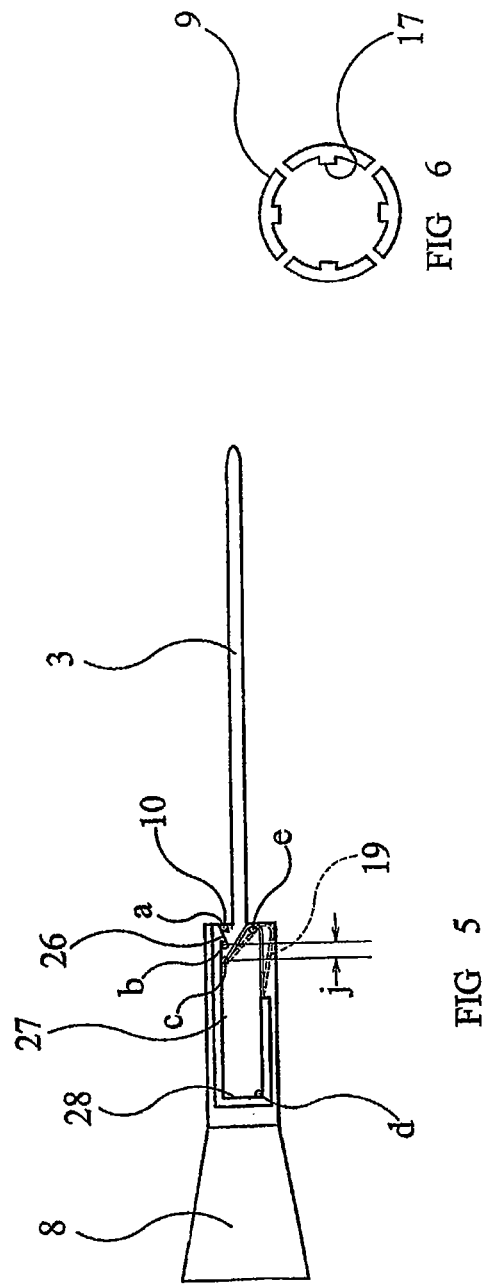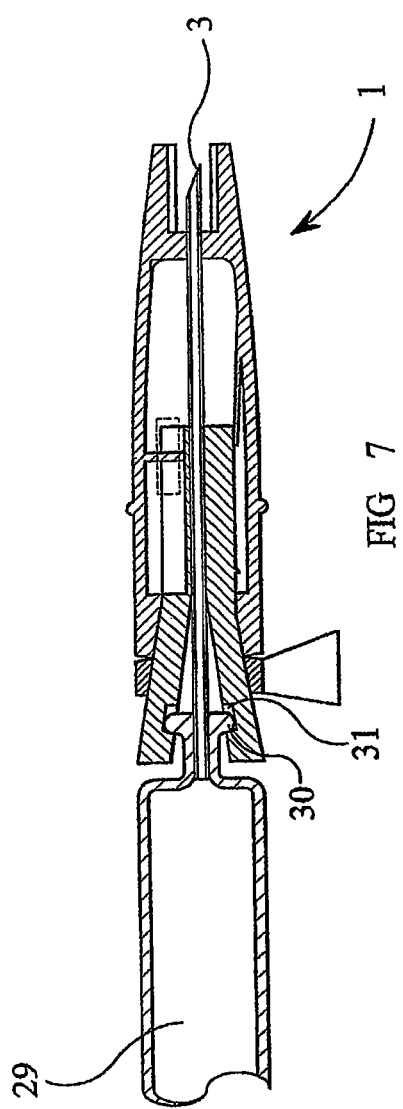

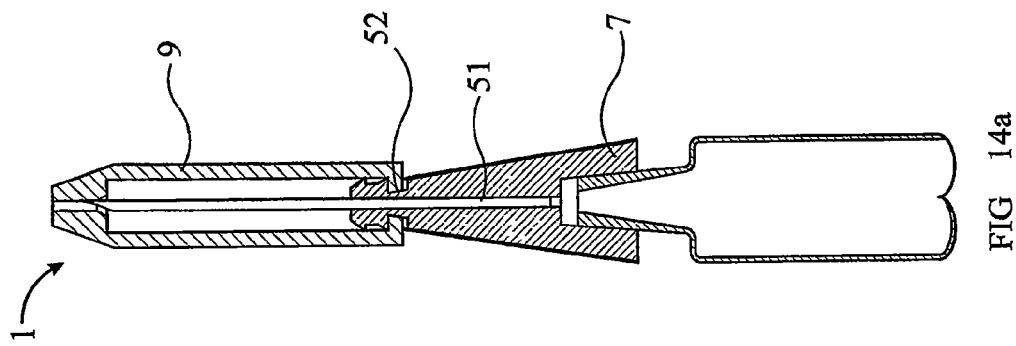
FIG 14a
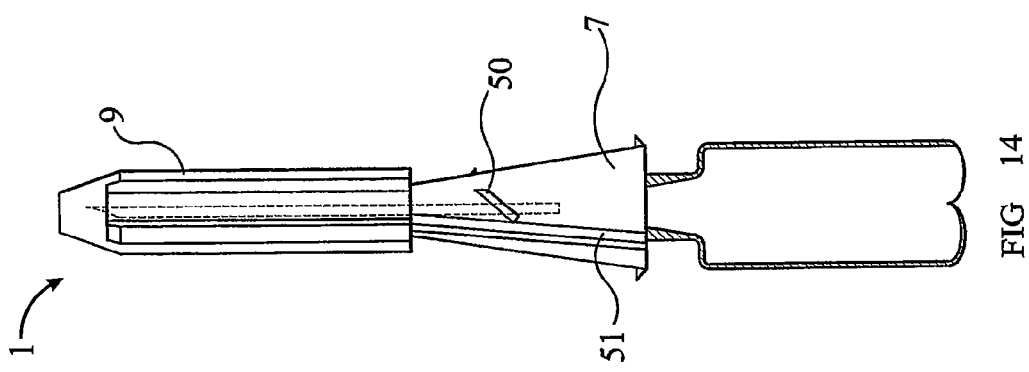
FIG 14
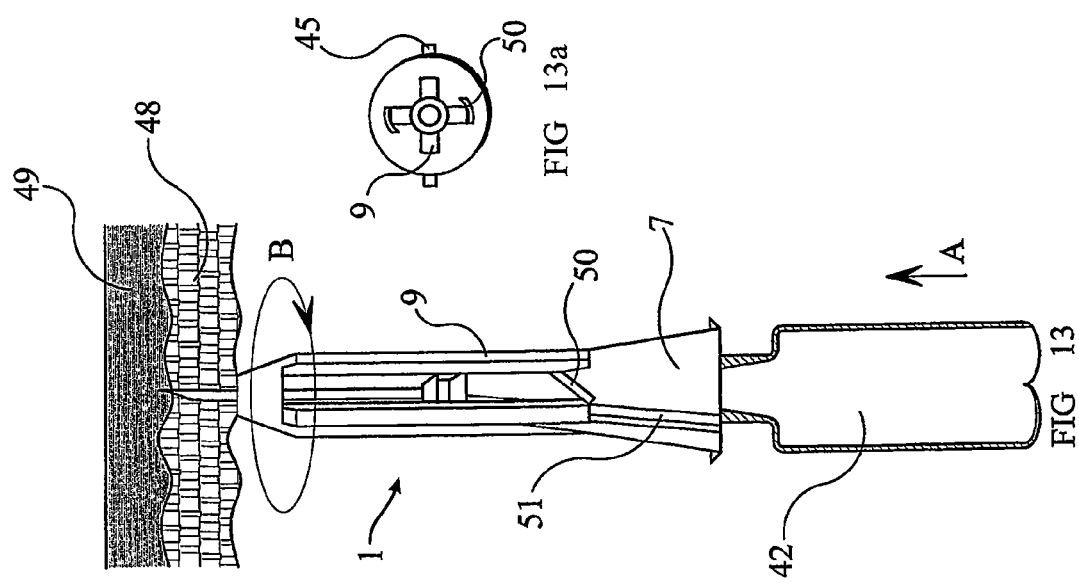
FIG 13a
FIG 13

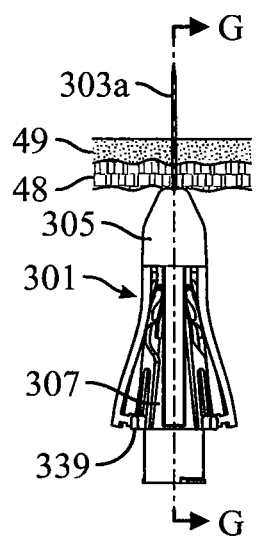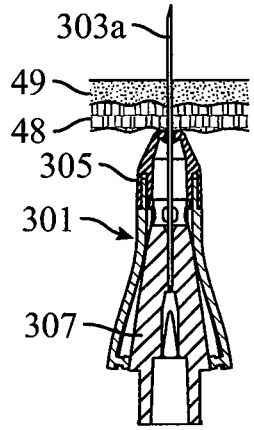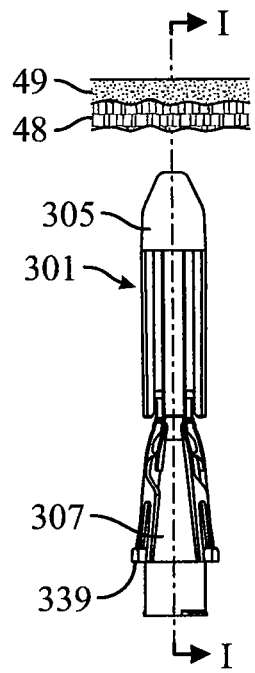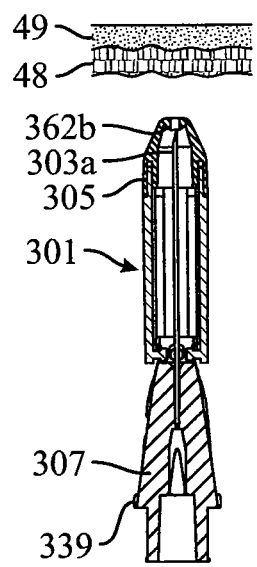
FIG. 25F    FIG. 25G    FIG. 25H    FIG. 25I
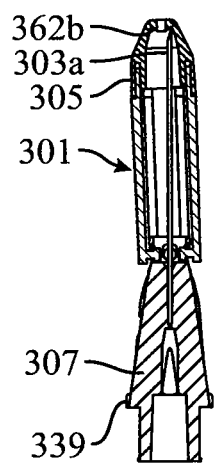
FIG. 25J

SAFETY NEEDLE

CROSS-REFERENCE TO RELATED APPLICATIONS

This application is a Continuation-In-Part application of U.S. patent application Ser. No. 11/815,475 filed Aug. 3, 2007 which is a Section 371 of International Application No. PCT/GB2005/000357, filed Feb. 3, 2005, which was published in the English language on Aug. 10, 2006, under International Publication No. WO 2006/082350 A1 and the disclosures of each of which are incorporated herein by reference.

BACKGROUND OF THE INVENTION

This invention relates to a safety needle, particularly a safety needle for automatically covering a needle following removal of the needle from a patient and a packing sleeve for setting the safety needle in a ready-to-use configuration by the act of removing the packing sleeve.

Needle stick injuries carry a significant risk of spreading infection, such as HIV and hepatitis, and are commonplace among healthcare workers. The United States of America has led the way in introducing legislation that obliges healthcare providers to use the safest devices when giving injections, intravenous drug administration and similar invasive procedures. Other countries are following and, even without legislation, the ever-present risk of litigation has alerted pharmaceutical companies and health authorities to seek suitable safe devices.

As a result of the heightened awareness of needle stick injuries, there have been a large number of medical devices directed to concealing or otherwise protecting the user and/or patient from an inadvertent needle stick. Such medical device often take the form of a protective sleeve which covers the tip of the needle after the injection has been given, or means for retracting the needle rapidly into the syringe barrel. Such safety needles are exemplified by U.S. Pat. No. 4,911,693, U.S. Pat. No. 4,813,940 and U.S. Pat. No. 5,104,384.

What is desirable is a safety needle that automatically covers a needle following removal of the needle from a patient. Further, it is desirable that the safety needle reliably slide into a locked position following removal, be securely retained in the locked position, indicate whether or not the safety needle is in the locked position and have a sufficiently spring biased slidable sleeve.

Additionally, medical devices used to deliver a drug to a patient, will often need to be activated or repositioned from an initial storage or shipping state to an intermediate, activated or primed position before use. Safety needles for example, often require for the tip of the needle to be visible prior to giving the injection because frequently a small amount of drug must be aspirated to clear out trapped air, and the volume must be corrected after drawing up the drug from a bulk container. Also, two of the most common types of injection given are intradermal and intravenous, and both require that the tip of the needle be at least partially visible to ensure that the tip of the needle is inserted into the tissues or vein bevel-side up. Because safety needles often utilize a spring force to extend a cover over the needle following injection that may creep or lose its resiliency over time, the safety needle is desirably stored in an initial, extended position with little or no force on the spring and then, during preparation of the medical device prior to use, the spring is compressed or otherwise activated. Because a protective cap may be removed prior to activation, needle sticks may occur while attempting to activate the device.

What is desirable is a packing sleeve covering an injection device that activates the injection device through the removal of the packing sleeve from the injection device.

BRIEF SUMMARY OF THE INVENTION

Briefly stated, the present invention is directed to a packing sleeve for use with a safety needle that automatically covers a tip of a needle following removal of the needle from a patient. The packing sleeve includes a generally hollow body having a longitudinal axis and a distal end and an open proximal end. The body surrounds at least a portion of the safety needle and has at least one track having an activation leg and a releasing leg. The at least one track is in sliding engagement with at least one member of the safety needle such that the motion of a portion of the safety needle relative to the body is dictated by a path the at least one member follows along the respective at least one track. The safety needle is in an initial position when the at least one member is proximate a first end of the activation leg and in an intermediate position when the at least one member is proximate a second end of the activation leg. The releasing leg extends from the second end of the activation leg and allows the at least one member to be slid toward and then removed from the proximal end of the body.

In another aspect, the invention is directed to a safety needle for automatically covering a tip of a needle following removal of the needle from a patient. The safety needle includes an injection device having an initial position and an intermediate position. A packing sleeve has a generally hollow body surrounding at least a portion of the injection device in the initial position and the intermediate position. The body is only removable from the injection device when the injection device is in the intermediate position.

In another aspect, the invention is directed to a safety needle for automatically covering a tip of a needle following removal of the needle from a patient. The safety needle comprises a hollow needle having a tip for injecting into the patient and a longitudinal axis. A hub is mounted to the needle and has an outer surface, a receiving end distal to the tip of the needle and an injection end proximal to the tip of the needle. The injection end has at least one recess. At least part of the outer surface of the hub tapers inwardly toward the injection end. A slidable sleeve has a mounting end distal to the tip of the needle and an injection end proximal to the tip of the needle. The tip of the needle is located inside the slidable sleeve in an extended position and the tip of the needle projects from the slidable sleeve in a retracted position. At least one projection having an enlarged distal width and a reduced proximal width extends radially inwardly from the mounting end and is slidably mounted to the hub between the receiving and injection ends of the hub in an initial position. The outer surface of the hub deflects the at least one projection and slidable sleeve outwardly in a radial direction as the slidable sleeve slides axially toward the receiving end of the hub. A displacement force urges the slidable sleeve from the initial position toward the retracted position generates a restoring force within the slidable sleeve. The restoring force urges the slidable sleeve to move toward the injection end of the needle hub and into the extended position upon removal of the displacement force. The at least one projection slides into and is retained within the at least one recess in the extended position.

In another aspect, the invention is directed to a safety needle for automatically covering a tip of a needle following removal of the needle from a patient. The safety needle comprises a hollow needle having a tip for injecting into the patient and a longitudinal axis. A hub is mounted to the needle and has an outer surface, a receiving end distal to the tip of the needle and an injection end proximal to the tip of the needle. At least part of the outer surface of the hub tapers inwardly toward the injection end. A slidable sleeve has a mounting end distal to the tip of the needle and an injection end proximal to the tip of the needle. The tip of the needle is located inside the slidable sleeve in an extended position and the tip of the needle projects from the slidable sleeve in a retracted position. The slidable sleeve is slidably mounted to the hub between the receiving and injection ends of the hub in an initial position. The outer surface of the hub deflects the slidable sleeve outwardly in a radial direction as the slidable sleeve slides axially toward the receiving end of the hub. The outer surface deflects the slidable sleeve in a radial direction as the slidable sleeve slides toward the receiving end of the hub. A displacement force urges the slidable sleeve from the initial position toward the retracted position generating a restoring force within the slidable sleeve. The restoring force urges the slidable sleeve to move toward the injection end of the needle hub and into the extended position upon removal of the displacement force. The indicator marking is covered by the slidable sleeve in the initial and retracted positions and visible in the extended position.

In another aspect, the invention is directed to a safety needle for automatically covering a tip of a needle following removal of the needle from a patient. The safety needle comprises a hollow needle having a tip for injecting into the patient and a longitudinal axis. A hub is mounted to the needle and has an outer surface, a receiving end distal to the tip of the needle and an injection end proximal to the tip of the needle. At least part of the outer surface of the hub tapers inwardly toward the injection end. The hub has at least one catch having a cammed surface. The outer surface of the hub proximate the at least one catch decreases in radial dimension moving circumferentially from the catch. A slidable sleeve has a mounting end distal to the tip of the needle and an injection end proximal to the tip of the needle. The tip of the needle is located inside the slidable sleeve in an extended position and the tip of the needle projects from the slidable sleeve in a retracted position. The slidable sleeve is slidably mounted to the hub between the receiving and injection ends of the hub in an initial position. The outer surface of the hub deflects the at least one projection and slidable sleeve outwardly in a radial direction as the slidable sleeve slides axially toward the receiving end of the hub. A displacement force urges the slidable sleeve against the cammed surface to twist the slidable sleeve relative to the hub and urges the slidable sleeve from the initial position toward the retracted position generating a restoring force within the slidable sleeve. The restoring force urges the slidable sleeve to move toward the injection end of the needle hub and into the extended position upon removal of the displacement force. The at least one projection slides into and is retained within the at least one recess in the extended position.

In another aspect, the invention is directed to a safety needle for automatically covering a tip of a needle following removal of the needle from a patient. The safety needle comprises a hollow needle having a tip for injecting into the patient and a longitudinal axis. A hub is mounted to the needle and has an outer surface, a receiving end distal to the tip of the needle and an injection end proximal to the tip of the needle. The injection end has at least one recess. At least part of the outer surface of the hub tapers inwardly toward the injection end. A slidable sleeve has a mounting end distal to the tip of the needle and an injection end proximal to the tip of the needle. The injection end has a needle opening and an axially extending interior ridge proximate the needle opening. The tip of the needle being located inside the slidable sleeve in an extended position and the tip of the needle projecting from the slidable sleeve in a retracted position. At least one projection extending inwardly from the slidable sleeve is slidably mounted to the hub between the receiving and injection ends of the hub in an initial position. The outer surface of the hub deflects the at least one projection and slidable sleeve outwardly in a radial direction as the slidable sleeve slides axially toward the receiving end of the hub. A displacement force urges the slidable sleeve from the initial position toward the retracted position generating a restoring force within the slidable sleeve. The restoring force urges the slidable sleeve to move toward the injection end of the needle hub and into the extended position upon removal of the displacement force. The at least one projection slides into and is retained within the at least one recess in the extended position. Displacing the slidable sleeve radially in the extended position causes the tip of the needle to extend into the ridge of the slidable sleeve.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1 is a side elevational view of a safety needle attached to a syringe without a packing sleeve in accordance with a preferred embodiment of the present invention;

FIG. 2 is a center-line cross sectional view of the safety needle and syringe shown in FIG. 1;

FIG. 3 is a center-line cross sectional view of the slidable sleeve of the safety needle shown in FIG. 2 with the slidable sleeve partly retracted to expose the hollow needle;

FIG. 4 is a center-line cross sectional view of the safety needle shown in FIG. 2 with the slidable sleeve in an extended and locked position;

FIG. 5 is a partial side elevational view of a detent mechanism of the safety needle needle shown in FIG. 1;

FIG. 6 is a bottom plan view of the receiving end of the slidable sleeve of the safety needle shown in FIG. 1 showing the cantilever arms;

FIG. 7 is a center-line cross sectional view of the safety needle shown in FIG. 2 attached to the barrel of a typical glass syringe used commonly for pre-filling with a drug;

FIG. 13 is a partial side cross-sectional view of the safety needle shown in FIG. 9 during injection into a patient;

FIG. 13a is a top plan view of the safety needle shown in FIG. 13;

FIG. 14 is a partial side cross-sectional view of the safety needle shown in FIG. 9 in an extended position following injection with the protective slidable sleeve locked in the extended position to cover the tip of the needle;

FIG. 14a is a centre-line cross-sectional view of the safety needle shown in FIG. 9 showing part of the locking mechanism;

FIG. 25F is a side elevational view of the safety needle shown in FIG. 25A injected into a patient and in the retracted position;

FIG. 25G is a cross sectional view of the safety needle shown in FIG. 25F taken along line G-G;

FIG. 25H is a side elevational view of the safety needle shown in FIG. 25A following removal from a patient in the extended position;

FIG. 25I is a cross sectional view of the safety needle shown in FIG. 25H taken along line I-I; and FIG. 25J is a cross sectional view of the safety needle shown in FIG. 25I with the slidable sleeve in a tilted and locked position.

DETAILED DESCRIPTION OF THE INVENTION

Figure 8:
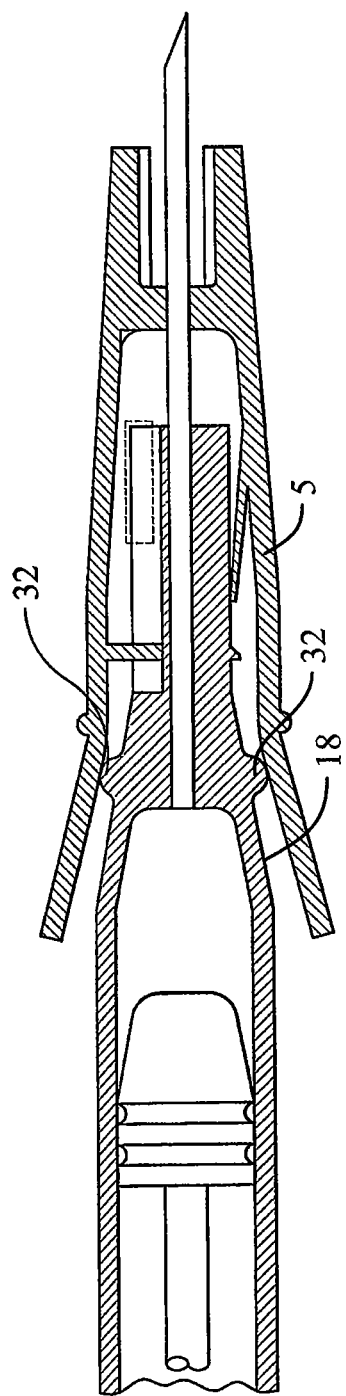
FIG. 8 is a cross-sectional view of an integral syringe barrel and needle hub in accordance with another embodiment of the present invention.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the safety needle, packing sleeve and designated parts thereof. Unless specifically set forth herein, the terms "a", "an" and "the" are not limited to one element but instead should be read as meaning "at least one". The terminology includes the words noted above, derivatives thereof and words of similar import.

Referring to the drawings, wherein like numeral indicates like elements throughout, there is shown various embodiments of a safety needle 1 and corresponding covers or packing sleeves 35, 135, 235. FIGS. 1-8 exemplify a safety needle 1 for preventing needle stick injuries which is suitable for use with the packing sleeve 35 of the present invention. FIG. 1 shows the general arrangement of a safety needle 1 (i.e. the safety needle accessory and the needle 3) of the type which may be used with the present invention as fitted to a male Luer taper connector 4 of syringe 2, with the end of the hollow (e.g. hypodermic) needle 3 enclosed by the slidable sleeve 5. The slidable sleeve 5 is prevented from longitudinal movement on the needle hub or hub 7 by a locking ring 13, which may be removed by pulling on the tab 14. The removable locking ring 13 may be connected to the needle hub 7 and/or the slidable sleeve 5. Although embodied in the drawings as cylindrical, the cylindrical shape of the needle hub 7 and slidable sleeve 5 may be replaced by triangular, rectangular or other shapes to suit the application.

FIG. 2 is a cross-section through the longitudinal axis of the safety needle 1. The needle hub 7 is cylindrical and terminates at the end which receives the syringe 2 with a conical section 8, and is molded onto the needle 3. The conical section 8 has an inner female Luer cone 24 which is shown frictionally attached to the male Luer cone 4 of syringe 2 (the Luer system for attaching the needle 3 to the syringe 2 has two main forms, that is a taper friction fit and a screw thread and both are included in the present invention). The cylindrical slidable sleeve 5 shrouds the needle 3 and the needle hub 7, and is freely sliding on and guided by the needle hub 7. At the receiving end (i.e. the end which receives the syringe) of slidable sleeve 5, there are four cantilever arms 9 which bear resiliently upon the surface 18 of the conical section 8. The slidable sleeve 5 is free to slide on the needle hub 7, but is temporarily prevented from doing so by the locking ring 13. The locking ring 13 is integrally molded with the slidable sleeve 5 by a frangible joint 15, and may be partially or wholly detached by pulling on the tab 14 to break the frangible joint 15. It is preferred that the ring 13 remains attached to the slidable sleeve 5 to reduce the number of discarded parts. In addition, the frangible joint provides a tamper-evident lock. Alternatively, the locking ring 13 may be molded to the needle hub 7 via a suitable frangible connection. When the locking ring 15 is removed, as shown in FIG. 3 the slidable sleeve 5 may be pushed in the direction of arrow X by acting on the face 6, and moves relative to the needle hub 7 to expose the needle 3. As the slidable sleeve 5 moves, the cantilever arms 9 are forced outwards by the surface 18 of the conical section 8. The cantilever arms 9 are resilient and the reaction force against the surface 18 produce a resultant force Y acting against arrow X, so that when the original force is removed, the slidable sleeve 5 returns to cover the tip of needle 3.

Since the resultant force is provided by the slidable sleeve 5 itself, no separate spring, e.g. a helical spring, is required in this embodiment although a separate spring could be used if desired. Thus, the resultant force may be generated within the slidable sleeve 5, for example by the slidable sleeve 5 having an elastically deformable portion, and/or by the safety needle 1 further comprising an elastically deformable member, such as a spring.

As shown in FIG. 6, the cantilever arms 9 may have pads 17 or radially inwardly extending projections, which bear onto the surface 18 and, by suitably designing the bearing surfaces of the pads 17, various spring characteristics may be obtained. Although four cantilever arms 9 are shown, any number of cantilever arms 9 could be employed. At least one cantilever arm 9 is required for this embodiment although 2-6 cantilever arms 9, and preferably four cantilever arms 9, are preferred.

Although the surface 18 of the hub 7 is exemplified by a conical surface, other embodiments may be used within the scope of the present invention. In the Figs., the surface 18 is straight, i.e. substantially conical by which the applicant means sufficiently conical to generate a resultant force, however, the surface need not be straight as shown, but may be curved to give a more linear return rate. Thus the force Y could be substantially constant over a reasonable working stroke of the slidable sleeve 5. In addition, the whole surface 18 of the receiving end of the needle hub 17 need not be conical. In fact, just one tapered section, e.g. a tapered ridge, would be sufficient. The tapered section does not have to project from the surface of the needle hub 7. The tapered section could also descend into the wall of the needle hub, i.e. a tapered detent rather than a tapered ridge. Also, as described below with reference to FIG. 8, provided the slidable sleeve 5 is suitably configured, a projection in the surface 18 of the needle hub 7 will suffice.

The different arrangements provide a great deal of design flexibility in the safety needle 1. For example, the linearity of the return rate may be varied depending on the particular requirements for a particular application.

Referring to FIGS. 3 and 4, when the slidable sleeve 5 returns in direction Y, it travels slightly past its original starting position, so that the resilient pawl 20 which was depressed by the surface 25 of hub 7, snaps out to act against face 16 of the hub 7. This ensures that the slidable sleeve 5 cannot be pushed back towards the syringe 2, and therefore the needle 3 is safely and securely covered. It is preferred that there is a pre-load between the cantilever arms 9 and hub 7 to ensure that the slidable sleeve 5 is sufficiently biased in the direction of arrow Y to complete its full displacement potential.

The slidable sleeve 5 preferably has a first extended position or initial position where the slidable sleeve 5 is able to be moved towards the receiving end of the needle hub 7 and a second extended position where the slidable sleeve 5 is in a locked position. The different start and finish positions of the slidable sleeve 5 is achieved by a detent mechanism shown in FIG. 5, which is to be read in conjunction with FIGS. 2, 3 and 4. After the first two or three millimeters of movement, a detent integral with the slidable sleeve "switches" so that the return of the slidable sleeve trips a latching pawl, so that the slidable sleeve returns only to the "safe" position; that is the pawl prevents the slidable sleeve from being moved towards the syringe a second time, and thus protects the tip of the needle. As part of the detent mechanism, an inside surface of the slidable sleeve has a pin 10 which engages a sprag 26 and a resilient pawl 19 attached to the needle hub 7 thereby holding the slidable sleeve in the first extended position and, in use, allowing the slidable sleeve to move into the second extended position. The pin 10 is integral or attached to the slidable sleeve 5. The sprag 26, resilient pawl 19, and recess 27 are molded integrally with the needle hubs 7, 8, and the pin 10 extends into the recess, and allowed to move freely except where controlled by the detent and the boundaries of the recess. In the initial assembly of the safety needle, the slidable sleeve 5 is placed over the needle 3 with pin 10 proximate to the sprag 26 (formed as part of the needle hub 7) at position a (FIG. 5). As the slidable sleeve 5 is moved further, the pin 5 deflects the resilient pawl 19, until the pin 10 is trapped behind sprag 26 at position b. In this position the slidable sleeve 5 is trapped on the needle hubs 7, 8 and cannot be removed without applying considerable force. This is the position of the components as supplied to the end user, and the location of the locking ring 13 takes account of this. With the locking ring 13 removed, the slidable sleeve 5 is pushed further towards the syringe 2, and the pin 10 again deflects the resilient pawl 19 until the pin 10 reaches position c. This distance j defines the initial displacement of the slidable sleeve 5, when starting the injection, and the tip of needle 3 may be level with the face 6 of slidable sleeve 5. The slidable sleeve 5 may now be moved towards the syringe until the pin 10 reaches the end wall 28 of the recess 27 at position d. This position defines the maximum displacement of slidable sleeve 5, and thus the maximum exposure of the needle 3. At any time the force acting on slidable sleeve 5 is removed, the slidable sleeve 5 will return in the direction of arrow Y until pin 10 reaches the position e. The pin 10 also helps prevent the removal of slidable sleeve 5, but additionally the tooth 21 is now proximate to face 22 on a cantilever arm 9, which prevents the removal of the slidable sleeve 5. In this final position, the pawl 20 engages with face 16 of hub 7 and prevents the slidable sleeve 5 from being moved. It should be noted that with the present diagrammatic presentation of the safety needle 1, a small amount of rotational movement is necessary between the slidable sleeve 5 and hub 7 to permit the pin 10 to move from position c to position e, but the rotation is preferably negligible.

The detent mechanism is interchangeable between the slidable sleeve 5 and needle hub 7 if required. Also, the detent mechanism described hereinabove is but one of a number of such mechanisms, the main requirement being to permit the following sequence of operation: permit the slidable sleeve to be moved sufficiently so that the opening in the slidable sleeve is level with or just in front of the tip of the needle 3, at which position the detent must be activated so that if the displacing force on the slidable sleeve 5 is removed, the slidable sleeve 5 slides forward and locks, thus protecting the user from contact with the tip of the needle 3. Typically, the tip of the needle 3 would be about 3 mm back from the face of the opening in the slidable sleeve 5 at the start, and 1 mm back from the face when the detent is activated.

FIG. 7 shows the device 1 as previously described, except that in this embodiment the needle 3 is bonded into the outlet end of the syringe barrel 29. The needle 3 is free to pass through the needle hub 7, and the cone 9 is adapted at 31 to snap-fit over the projection 30. The form of projection 30 is produced as a result of rolling the glass onto a mandrel, whereby the excess glass is forced in to the shape as shown. Alternatively, a more defined snap-fitting termination may be formed, the object being to make the safety needle 1 difficult to remove after assembling it to the syringe barrel.

FIG. 8 shows a safety needle 1 in which the needle hub 7 is integral with the barrel of the syringe 2. The slidable sleeve 5 is then attached to the needle hub 7 in the manner as described hereinbelow. The material of the needle hub 7, which also constitutes the barrel of the syringe 2, would, of course, have to be made from a drug-compatible material.

As mentioned hereinabove, FIG. 8 also shows the separate feature of the projection 32 on the surface 18 of the needle hub 7 which may be used to deflect the slidable sleeve 5 thereby generating the resultant force. This embodiment, i.e. incorporating the projection 32, provides a highly non-linear return rate since the length of the slidable sleeve 5 is effectively reduced as the slidable sleeve 5 and the needle hub 7 are slid together, thereby increasing the stiffness of the slidable sleeve 5.

As an alternative to the tapered outer surface of the needle hub 7, the slidable sleeve 5 may have at least one cantilever arm 9 which engages a helical track in the outer surface of the needle hub 7 such that, in use, as the needle 3 is inserted into a patient, the at least one cantilever arm 9 is displaced radially by the helical track in the outer surface of the needle hub 7 thereby generating the resultant force. Thus, as the slidable sleeve 5 is caused to move towards the receiving end of the needle hub 7, one or more cantilever arms 9 are forced to follow the direction of the helical tracks. Since the cantilever arms 9 are resilient, a resultant force will be generated.

As an alternative to cantilever arms 9, the receiving end of the slidable sleeve 5 itself may have elastic properties such that, in use, as the needle 3 is inserted into a patient, the resultant force is generated within the slidable sleeve 5. By elastic properties the applicant means that the resultant force is generated within a radially continuous slidable sleeve, i.e. a sleeve without cantilever arms 9. The elastic properties may be achieved by using an elastic material, such as an elastomeric polymer. Alternatively, the receiving end of the slidable sleeve 5 may be concertinaed, with the ridges, of course, running parallel to the hollow needle 3. The elastic properties could also be generated using a circumambient spring attached to the slidable sleeve 5.

As a further alternative, instead of the resultant force being generated in the slidable sleeve 5 itself, the safety needle may incorporate an alternative, or additional, resultant mechanism, such as a helical spring. Such safety needles are exemplified in U.S. Pat. No. 4,911,693, U.S. Pat. No. 4,813,940 and U.S. Pat. No. 5,104,384.

FIGS. 9-14a show an embodiment of the present invention in which the needle hub 7 and the slidable sleeve 5 are adapted to allow the slidable sleeve 5 to be retracted into and held at an intermediate position (FIG. 12) between the extended position (FIG. 9) and the retracted position (FIG. 13) such that, in use, the tip of the needle 3 projects partially from the slidable sleeve 5, that is the needle bevel is exposed. In this intermediate position the locking mechanism is not engaged and hence the slidable sleeve 5 may be retracted further into the (fully) retracted position as it is inserted into the patient. The advantages of this arrangement are that exposing the tip of the needle 3 partially allows the user to position the needle 3 more precisely on, for example, the patient's skin 48, and also facilitates the aspiration of trapped air and excess drug. The use of the pack 35 prevents needle stick injuries when the safety needle 1 is in the intermediate position.

Figure 9:
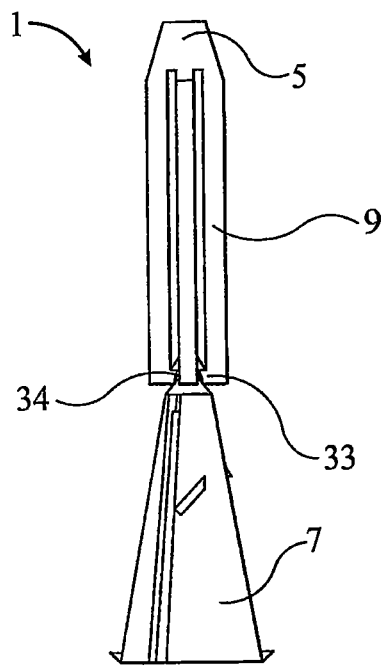
FIG. 9 is a side elevational view of a safety needle in accordance with another embodiment of the invention as assembled by the manufacturer, prior to inserting it into its pack.
Figure 9A:
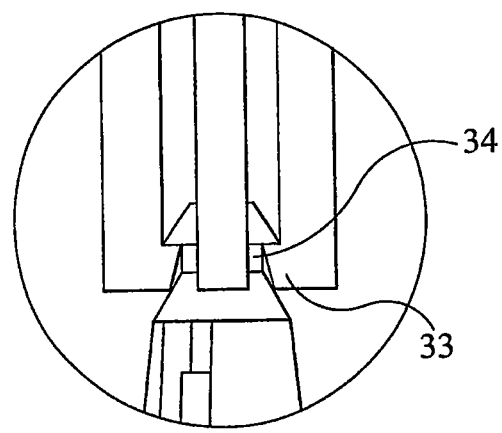
FIG. 9a is an enlarged side sectional view of the safety needle shown in FIG. 9.

FIG. 9 shows the device as assembled by the manufacturer, and comprises a needle hub 7, being of conical or other tapering form. The slidable sleeve 5 has cantilever arms 9 attached or integral, the arms 9 terminating with an radially inwardly extending projection 33, which engages with undercut 34 of the needle hub 7, shown in greater detail in FIG. 9a. In the position shown, there is little load on the spring cantilever arms 9, but sufficient to hold the components together.

Figure 10A:
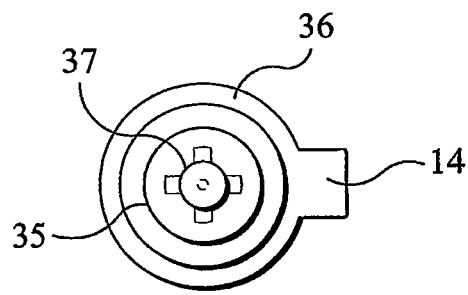
FIG. 10a is a top plan view of the safety needle shown in FIG. 10.
Figure 10:
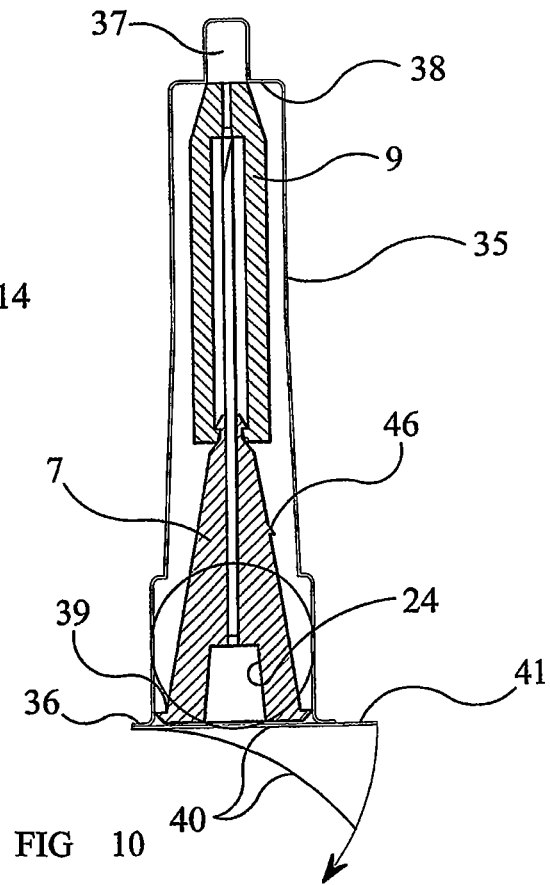
FIG. 10 is a center-line cross-sectional view Of the safety needle shown in FIG. 9 in its pack.

Referring to FIG. 10, this is a center-line cross-section through the safety needle assembled into its pack 35. The pack 35 is releasably mounted on the needle hub 7 and slidable sleeve 5, that is the safety needle 1 is held within the pack 35, for example by friction, but may be removed by the user. To facilitate the releasable mounting the pack 35 and safety needle 1 have engageable portions which may simply be the surfaces of the pack 35 and safety needle 1. These surfaces may be textured or have projections. The pack 35 is preferably tubular and also preferably made from a deep-drawn vacuum formed plastic material. The pack 35 is shown with a flange 36 and open at the receiving end of the needle hub 7, and closed at the injection end by the extension 37. The inner face of shoulder 38 rests on the end face of the slidable sleeve 5. The needle hub 7 has one or more projections 39, which provide a light frictional retaining force on the inside of the pack 35 to prevent the safety needle 1 from falling out. The safety needle 1 may be further retained inside the pack 35 by a releasable (peel-off) membrane 40, which is preferably gas permeable. The membrane 40 is bonded to flange 36, and may be made from a porous material such as TYVEK® brand spunbonded olefin i.e., a spun-bonded high-density polyethylene available from DuPont and which is used extensively in pharmaceutical packaging to permit a sterilizing gas, such as ethylene oxide, to penetrate the pack 35 while preventing ingress of bacteria during storage. Other peelable materials may be used according to the sterilization process used. The membrane 40 may have a tag 41 to assist removal. The needle hub 7 has a syringe adaptor 24 which may be configured to suit the common Luer taper or threaded Luer lock syringe nozzles.

Figure 12A:
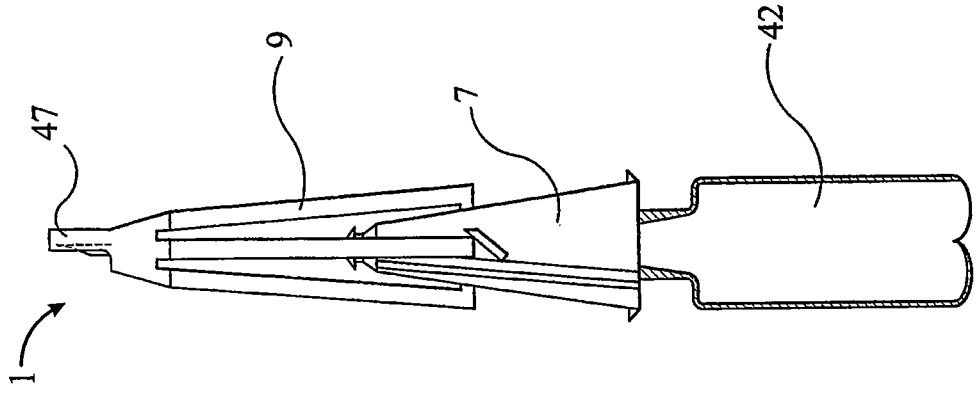
FIG. 12a is a partial side cross-sectional view of the safety needle shown in FIG. 12 with an alternative shroud to increase the protection against needle stick injuries, while allowing the needle bevel to be seen immediately prior to giving the injection.
Figure 12:
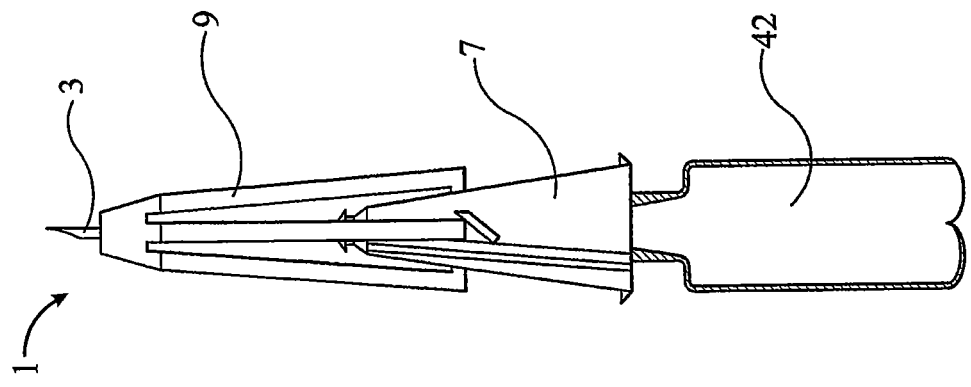
FIG. 12 is a partial side cross-sectional view of the safety needle shown in FIG. 9 in an initial position with the pack removed.
Figure 11:
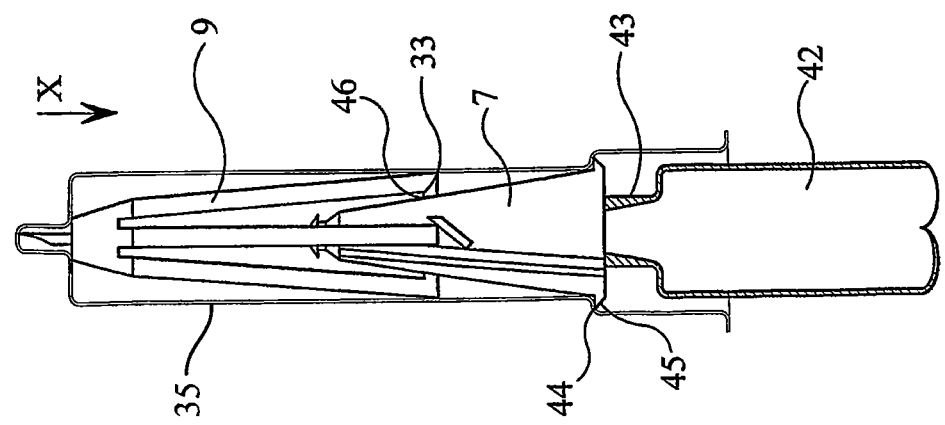
FIG. 11 is a partial side cross-sectional view of the safety needle shown in FIG. 9 showing how the pack is used to hold the safety needle when connecting it to a syringe.

Referring to FIG. 11, to assemble the safety needle 1 to a pre-filled syringe 42, the user removes the peelable membrane 40 by pulling on tag 41. Holding the packing sleeve 35, the user pushes the adaptor 24 of the needle hub 7 in the direction of the arrow X onto the syringe connector 43. This causes the inner face of the shoulders 38 to press against face of slidable sleeve 5 which moves towards the syringe 42. The injection end of the packing sleeve 35 has an extended portion which is capable of housing the tip of the needle 3 in the intermediate position and the shoulders 38 of the extended portion abut against the injection end of the slidable sleeve thereby causing the slidable sleeve 5 to move in to the intermediate position when the packing sleeve 35 is caused to move towards the receiving end of the needle hub 7. At the same time, the cantilever arms 9 are forced outwards as they travel up the surface of the needle hub 7, until the small shoulder 44 on the slidable sleeve 5 reaches the projection 45 on the needle hub 7, thus preventing further movement. At or about this point, at least one of the projections 33 snaps over a catch 46 on the needle hub 7. The cantilever arms 9 are now loaded radially, and exerting a resultant force urging the slidable sleeve 5 off the needle hub 7. The packing sleeve 35 may now be removed, and catch 46 prevents the slidable sleeve 5 from moving with respect to the needle hub 7 through the resultant force of the cantilever arms 9. With the packing sleeve 35 removed, the safety needle 1 will appear as shown in FIG. 12, and is ready for use. The tip needle 3 is thus partially exposed, i.e. the bevel of the needle may be seen by the user projecting from the slidable sleeve 5, and the user may aspirate trapped air and excess drug. FIG. 12a shows the safety needle 1 ready for use, as in FIG. 12, but with an extension 47 on face of slidable sleeve 5 extended to partially shroud the tip of the needle 3, which will afford more protection to the user and the patient prior to injection.

Referring to FIG. 13, the user then pushes the needle 3 in the direction of arrow A through the patient's epidermis 48 and into the subcutaneous tissue 49, which brings the face of the slidable sleeve 5 into contact with the stratum corneum of the patient's epidermis 48. Further movement in the direction of arrow A pushes the slidable sleeve 5 towards the syringe 42, and thus the cantilever arms 9 are forced further outwards by the conical surface of the needle hub 7. At the same time, the end of at least one cantilever arm 9 is forced against a cam 50 which causes the slidable sleeve 5 and cantilever arms 9 to rotate in the direction of arrow B, until the end of cantilever arm 9 drops into the groove 51. The groove 51 has a slope towards the needle 3, which maintains the resultant force of the cantilever arm 9. At this point, (which represents only a millimeter or two of movement of the slidable sleeve 5), if the needle 3 is withdrawn from the patient, the resultant force of the cantilever arms 9 urges the slidable sleeve 5 towards the tip of the needle 3 until the tip of the needle 3 is shielded by the slidable sleeve 5. At the end of travel of the projection 33 and the cantilever arm 9, the projection 33 on cantilever arm 9, which is still sliding in the groove 51, drops into the hole 52. This locks the slidable sleeve 5 in position and prevents the slidable sleeve 5 being pushed back towards the syringe 42, or being pulled off the needle hub 7. This position is shown in FIGS. 14 and 14a, the latter being a section through the center-line, and the safety needle rotated to show the grooves 51 and holes 52, with the projections 33 on cantilever arms 9 located within the holes 52. Although the lockably engaging projection 33 and hole 52 are shown with reference to cantilever arms 9, any slidable sleeve 5 may be locked into the extended position using one or more projections 33 and corresponding one or more holes 52. Such an arrangement results in a less complex, and hence less costly, safety needle 1 and avoids introducing opposing frictional and/or detent forces which result from an integral but independent locking mechanism. An advantage of the projection 33/hole 52 mechanism is that the locking mechanism provides substantially no resistance against the resultant force as the slidable sleeve 5 moves from the retracted position to the extended position. When the slidable sleeve 5 reaches the extended position the locking mechanism engages which then resists the resultant force.

The protective packing sleeve 35 confers safe storage and handling advantages, allows the safety needle 1 to be assembled to a syringe 42 without risking premature operation of the safety mechanism, and does not add to the overall cost of the device, since it is similar to the vacuum-formed covers already in use for needles and syringes. For the user, the operation of the safety needle is practically identical to the use of a standard needle.

It is preferable that the coefficient of friction between the slidable sleeve 5 and the needle hub 7 is low, so that the resultant biasing force to return the slidable sleeve 5 is not compromised by "stiction", or so high that the force required on the patient's skin to deflect the slidable sleeve 5 is excessive. This may be achieved by careful selection of materials. Such materials are known in the art, for example, the needle hub could be made from a high-density polyethylene or similar drug-compatible plastics material, and the slidable sleeve 5 from an inexpensive plastics material such as polycarbonate, polystyrene, polyester or PVC. A more expensive, highly creep-resistant plastics material, for example polyphenylene sulfone, could also be used. As an alternative, the slidable sleeve 5, or just the at least one cantilever arm 9, may be made from metal, preferably stainless steel. The metal would be fabricated sufficiently thinly to provide the required elastic properties. If necessary, a lubricant may be used, or a lubricant may be incorporated with the polymers. Generally the materials should be suitable for sterilization by gamma radiation, but it is possible to select materials compatible with sterilization by steam or other gas such as ethylene oxide.

In a preferred embodiment, the slidable sleeve 5, prior to use, is not under any substantial load. Any substantial load indicates a load which is sufficient to cause the material of the slidable sleeve 5 to undergo creepage during storage at ambient temperature.

Figure 15:
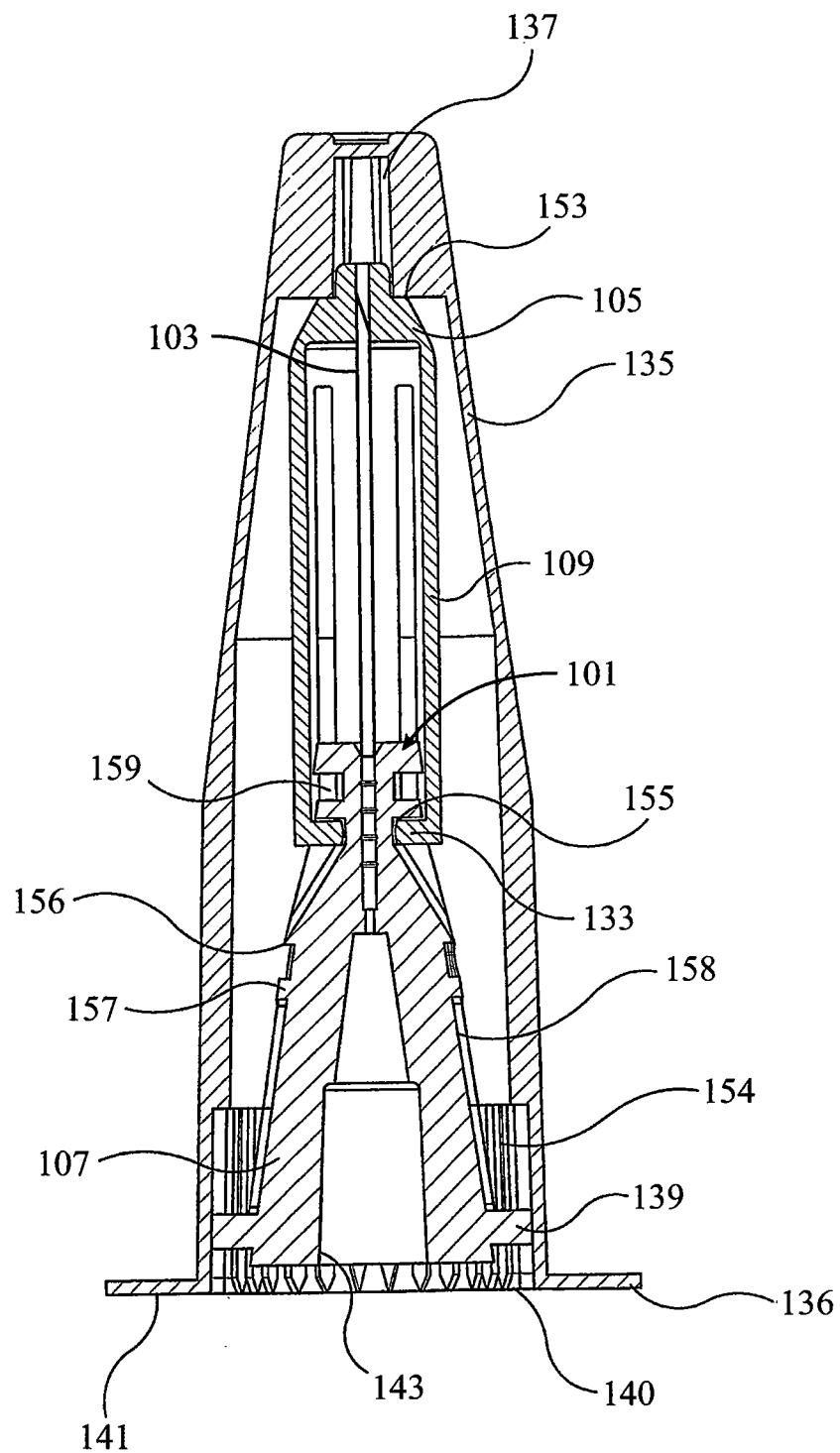
FIG. 15 is a cross sectional view of a safety needle and packing sleeve in accordance with another embodiment of the present invention.
Figure 16:
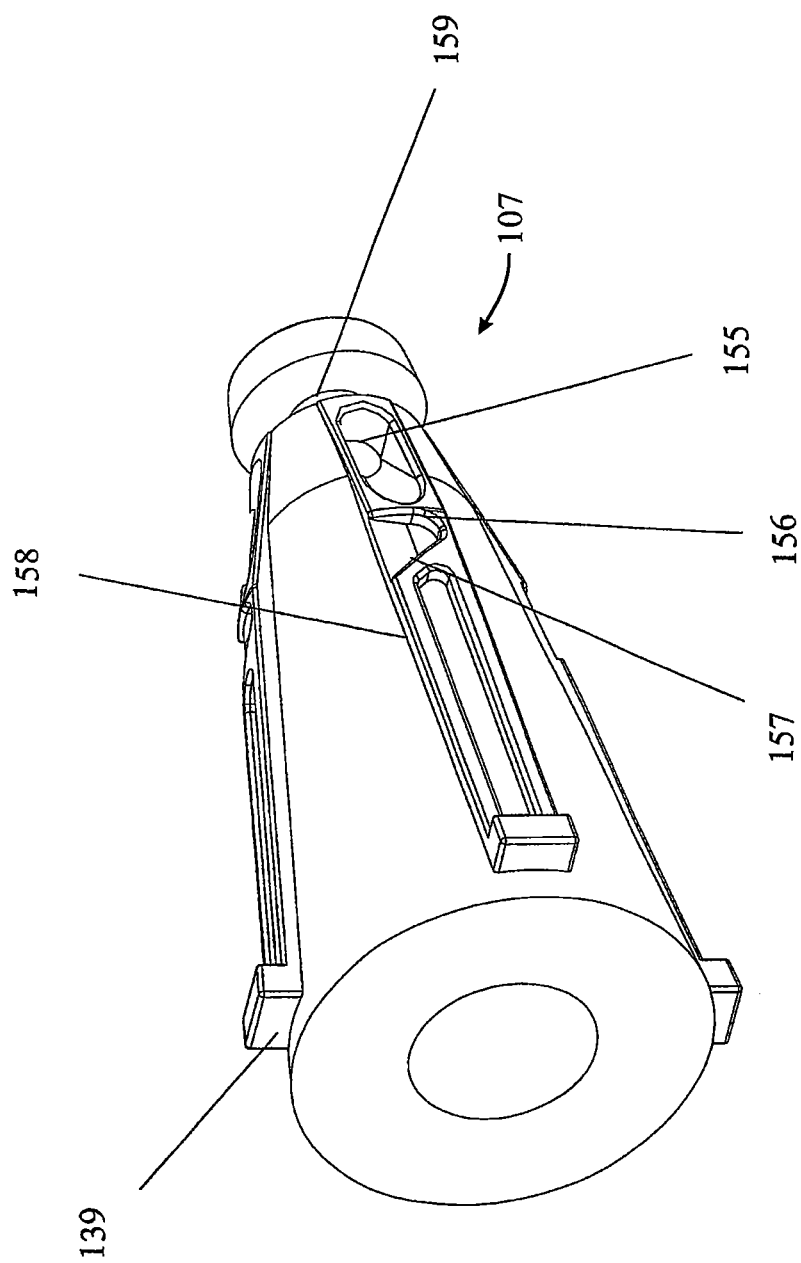
FIG. 16 is a perspective view of the hub of the safety needle shown in FIG. 15.

FIGS. 15 and 16 show a further embodiment of the present invention in which the needle hub 107 and the slidable sleeve 105 are adapted to allow the slidable sleeve 105 to be retracted into and held at an intermediate position (not shown) while the needle 103 is still contained within the packing sleeve 135. This embodiment further allows the safety needle 1 to be stored without any substantial load on the slidable sleeve 105 thereby preventing creepage during storage.

FIG. 15 shows a center-line cross-section through the safety needle 101 assembled into its packing sleeve 135 and FIG. 16 shows a three-dimensional representation of the needle hub 107. The packing sleeve 135 is releasably mounted on the needle hub 107 and slidable sleeve 105. The packing sleeve 135 is preferably tubular and also preferably made from a deep-drawn vacuum formed plastic material. The packing sleeve 135 is shown with a flange 136 and open at the receiving end of the needle hub 107, and closed at the injection end by the extension 137 defined by a plurality, e.g. six, ribs 153. The ribs 153 rest on the end face of the slidable sleeve 105. The needle hub 107 has one or more projections 139, which provide a light frictional retaining force on the inside of the packing sleeve 135 to prevent the safety needle 101 from falling out. The packing sleeve 135 may also have a partially textured internal surface 154 which engages the projections 139 in order to prevent rotation of the safety needle 101 within the packing sleeve 135. The safety needle 101 may be further retained inside the packing sleeve 135 by a releasable (peel-off) membrane 140 as described hereinabove. The needle hub 107 has a syringe adaptor 124 which may be configured to suit the common Luer taper or threaded Luer lock syringe nozzles.

In the position shown in FIG. 15, the safety needle 101 is as assembled by the manufacturer. The slidable sleeve 105 has cantilever arms 109 attached or integral, the arms 109 terminating with a projection 133, which engages with indent 155 of the needle hub 107. The indent 155 is of sufficient depth that the cantilever arms 109 are under substantially no load, i.e. the sleeve 105 is not radially expanded. In this position, the sleeve 105 is prevented from sliding off the needle hub 107 by the packing sleeve 135 and the engagement between the projection 133 on the cantilever arms 109 and the indent 155 on the hub 107.

To assemble the safety needle 101 to a pre-filled syringe 42, the user removes the peelable membrane 140 by pulling on tag 141. Holding the packing sleeve 135, the user pushes the adaptor 124 of the needle hub 107 onto the syringe connector 143. This causes the inner face of the ribs 153 to press against face of slidable sleeve 105 which moves towards the syringe (not shown in FIGS. 15-16). The injection end of the packing sleeve 135 is capable of housing the tip of the needle when the safety needle 101 is in the intermediate position. The ribs 153 of the packing sleeve 135 abut against the injection end of the slidable sleeve 105 thereby causing the slidable sleeve 105 to move in to the intermediate position when the packing sleeve 135 is caused to move towards the receiving end of the needle hub 107. The indent 155 has a tapering interior surface which causes the sleeve to expand radially as the sleeve 105 is caused to move up the surface of the needle hub 107. The sleeve 105 is caused to move until the sleeve 105 is in the intermediate position wherein the tip of the needle 103 is partially exposed. At or about this point, at least one of the projections 133 snaps over a catch 156 on the needle hub 107. The cantilever arms 109 are now loaded radially, and exerting a resultant force urging the slidable sleeve 105 down the needle hub 107. This resultant force is countered by the catch 156 on the hub 107. The packing sleeve 135 may now be removed, and catch 156 prevents the slidable sleeve 105 from sliding down the needle hub 107 through the resultant force in the cantilever arms 109. With packing sleeve 135 removed, the safety needle 101 is ready for use. The tip of the needle 103 is thus partially exposed, i.e. the bevel of the needle 103 may be seen by the user projecting from the slidable sleeve 105, and the user may aspirate trapped air and excess drug.

Once the safety needle 101 is in the intermediate position and the packing sleeve 135 is removed, the user then pushes the needle 103 through the patient's epidermis 48 and into the subcutaneous tissue 149, which brings the face of the slidable sleeve 105 into contact with the stratum corneum of the patient's epidermis 48 (See FIG. 13). Further movement of the needle 103 into the patient's skin 48 pushes the slidable sleeve 105 towards the syringe 142, and thus the cantilever arms 109 are forced further outwards by the conical surface of the needle hub 107. At the same time, the end of at least one cantilever arm 109 is forced against a cam 157 which causes the slidable sleeve 105 and cantilever arms 109 to rotate (in an analogous manner to FIG. 14), until the end of cantilever arm 109 is directed along the guide 158. As shown in FIG. 16, the catch 156 and the cam 157 are preferably formed into a single structure. The projection 133 follows guide 158 as the sleeve is caused to retract. As the sleeve 105 retracts, the sleeve 105 is deflected radially by the sloping of the hub 107 towards the needle 103.

At this point, (which represents only a millimeter or two of movement of the slidable sleeve 105), if the safety needle 101 is withdrawn from the patient, the resultant force of the cantilever arms 109 urges the slidable sleeve 105 towards the tip of the needle 103 until the tip of the needle 103 is shielded by the slidable sleeve 105. At the end of travel of the projection 133 and the cantilever arm 109, the projection 133 on cantilever arm 109, which is still following the guide 157, drops into the hole 159. This locks the slidable sleeve 105 in position and prevents the slidable sleeve 105 being pushed back towards the syringe 142, or being pulled off the needle hub 107.

The hole 159 is shown further towards the injection end of the hub 107 than the indent 155. This allows the hole 159 to be a circumferentially continuous hole which permits free rotation of the sleeve 105 around the hub in the locked position. This free rotation provides a more secure locked position. In a simple hole/projection arrangement, accidental rotation of the sleeve 105 might distort the sleeve 105 sufficiently to disengage the hole and projection. Allowing free rotation means that the rotation is not resisted preserving the integrity of the locking mechanism.

As previously mentioned hereinabove, the syringe may be supplied empty or pre-filled. When a pre-filled syringe is used, the syringe is preferably sealed using a sealing cap or plug to prevent evaporation or loss of the drug, excipient, carrier and/or diluent by, for example, thermal expansion.

As well as application to a syringe, the same safety needle 101 described herein could form the basis of a intravenous giving set, so that the insertion of the needle 103 into the patient's vein is simple and safe. Indeed, the safety needle 101 of the present invention may be used with any suitable injection device.

Referring to FIGS. 17-20, another embodiment of the packing sleeve, generally designated 235, is shown for use with a medical device, preferably the safety needle 101 as shown in FIGS. 15-16 and described above. In addition to the above described features, the safety needle 101 may additionally include a circular retaining ring (not shown) disposed around the cantilever arms 109 of the slideable sleeve 105 to retain the slideable sleeve 105 on the needle hub 107. The packing sleeve 235 prevents the safety needle 101 from being removed from the packing sleeve 235 without first activating or priming the safety needle 101 to move the safety needle 101 from the initial position to the intermediate position. Though it preferred that the medical device be the safety needle 101 it is within the spirit and scope of the present invention that the medical device be any injection or medical delivery device that has an initial position and an intermediate position as known by person having ordinary skill in the art in view of the packing sleeve 235 described further below.

The packing sleeve 235 includes a generally hollow body 270 has a distal end 270a and an open proximal end 270b. The body 270 surrounds at least a portion of the safety needle 101, preferably the entire safety needle 101, and the open proximal end 270b is initially preferably covered by a releasable membrane 240 such that the safety needle 101 is sealed within the packing sleeve 235. The membrane 240 is bonded to a flange 272 extending radially outwardly from the body 270 proximate the proximal end 270b. The membrane 240 is preferably gas permeable and may be made from a porous material such as TYVEK® brand spunbonded olefin i.e., a spun-bonded high-density polyethylene available from DuPont and which is used extensively in pharmaceutical packaging to permit a sterilizing gas, such as ethylene oxide, to penetrate the pack 235 while preventing ingress of bacteria during storage. Other peelable materials may be used according to the sterilization process used. The membrane 240 may have a tab or tag (not shown) to assist removal. The body 270 is preferably tubular and is made from a deep-drawn vacuum formed polymeric material but the body 270 may have any shape such as rectangular and may be comprised of any suitable material.

Figure 17:
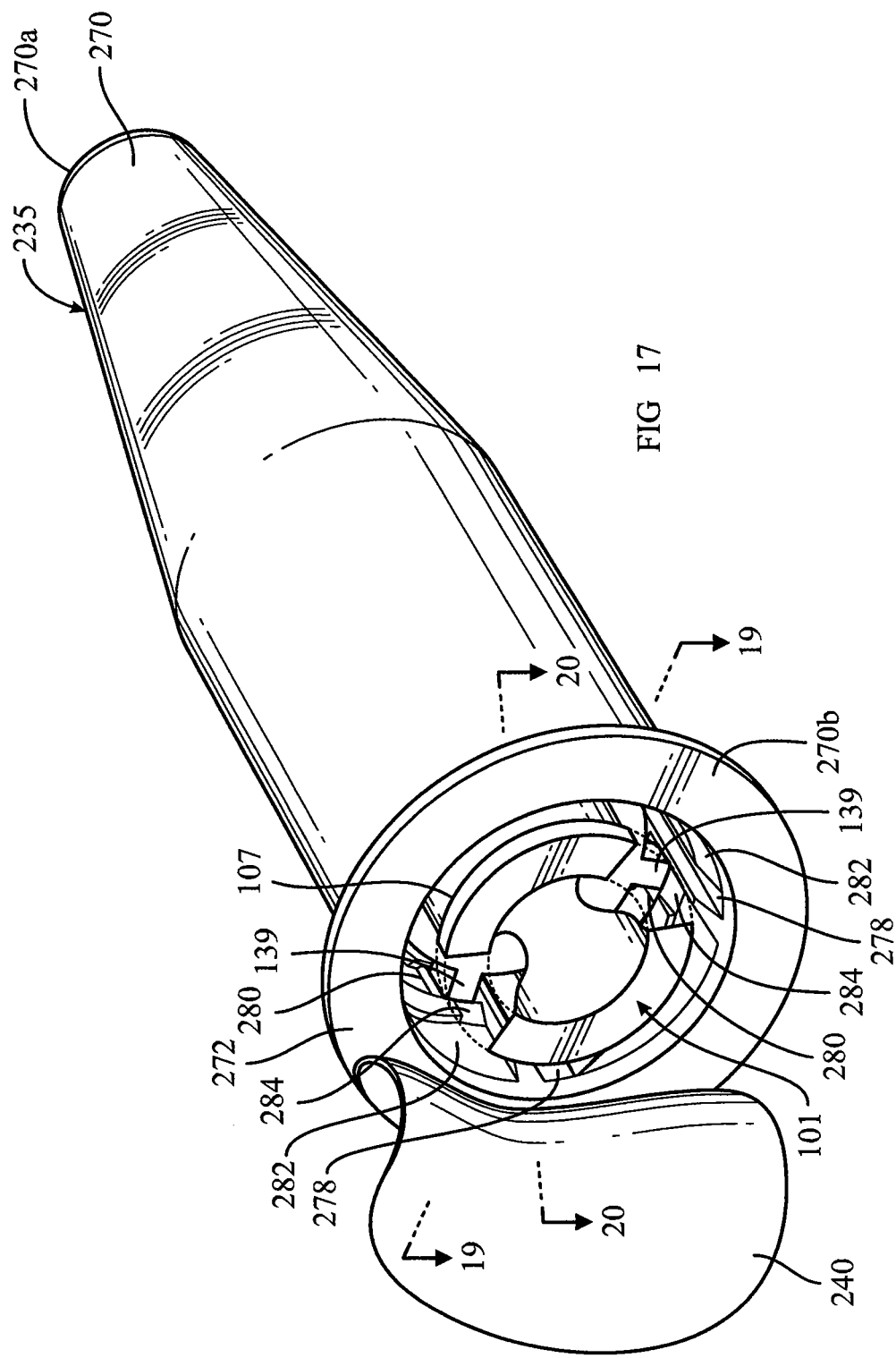
FIG. 17 is a perspective view of a safety needle and packing sleeve in accordance with another embodiment of the present invention with a releasable membrane partially removed.
Figure 18:
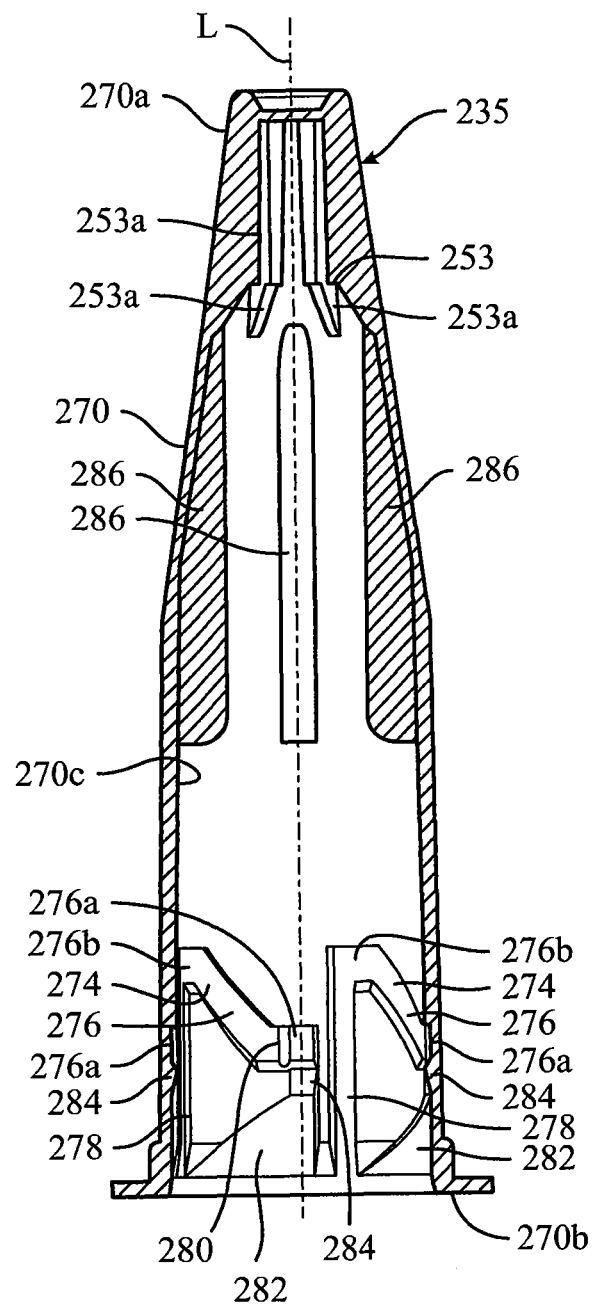
FIG. 18 is a cross-sectional view of the packing sleeve shown in FIG. 17 with the safety needle removed.

Referring to FIGS. 17 and 18, the body 270 has at least one, and preferably four tracks 274 that extend radially outwardly into the body 270 proximate the proximal end 270b of the body 270. However, the tracks 274 may extend radially inwardly from the body 270 or be formed by ridges that extend radially inwardly from the body 270. It is preferred that the tracks 274 be equally circumferentially spaced around an interior surface 270c of the body 270 that correspond to the plurality of members or projections 139 extending from the needle hub 107. Though it is preferred that the projections 139 engage with the corresponding tracks 274, the member or projection 139 may be any portion of the needle hub 107 is in contact with the body 270. The tracks 274 are in sliding engagement with the projections 139 such that the motion of the needle hub 107 relative to the body 270 is dictated by a path the projections 139 follow along the tracks 274 while the slideable sleeve 105 is prevented from moving toward the distal end 270a of the body 270 by a ledge 153. The ledge 153 is preferably comprised of a plurality of ribs 153a that form a cavity 137 for receiving the needle 103 when the safety needle 101 is in the intermediate position.

Referring to FIG. 18, the tracks 274 each have an activation leg 276 and a releasing leg 278. The activation leg 276 is preferably slanted or angled with respect to a longitudinal axis L of the body 270 such that the activation leg 276 has a horizontally extending direction. Alternatively, the activation leg 276 may be stepped such that the vertical and horizontal directions are separated. The activation leg 276 preferably has a retaining bump 280 (FIG. 17) that extends generally parallel to the longitudinal axis L of the body 270 and projects radially inwardly from the track 274 and is proximate a first end 276a of the activation leg 276. The activation legs 276 also each preferably have an assembly path 282. The assembly paths 282 and the first ends 276a of the activation legs 276 are preferably separated by a ramp 284 that is inclined toward the distal end 270a of the body 270. The assembly paths 282 are preferably generally triangular in shape and encompassed the portions of the proximal end 270b between the releasing legs 278, such that during assembly, the projections 139 extending from the needle hub 107 are directed toward and aligned with the corresponding ramps 284. The assembly paths 282 help to ensure that the safety needle 101 is properly inserted into the body 270. The projections 139 are then urged over the ramps 284 with a predetermined amount of force such that the projections 139 snap fit into the first ends 276a of the activation legs 276 and the ramps 284 and the retaining bumps 280 retain the projections within the first ends 276a of the activation legs 276.

The body 270 preferably includes at least one, and preferably four, retaining ribs 286 between the tracks 274 and the distal end 270a of the body 270. The retaining ribs 286 preferably extend the length of cantilever arms 109 but the retaining ribs 286 may extend any length so long as they are proximate the cantilever arms 109 when the safety needle 101 is in the initial position. The retaining ribs 286 preferably extend in the axial direction and project radially inwardly from the interior surface 270c of the body 270. Each retaining rib 286 is preferably circumferentially aligned with the first end 276a of a respective activation leg 276 such that each retaining rib 286 is proximate and circumferentially aligned with a respective cantilever arm 109 when the safety needle 101 is in the initial position. The retaining ribs 286 are preferably spaced between, or unaligned with, the cantilever arms 109 when the safety needle 101 is moved out of the initial position (i.e. twisted relative to the packing sleeve 235) as described further below.

Figure 19:
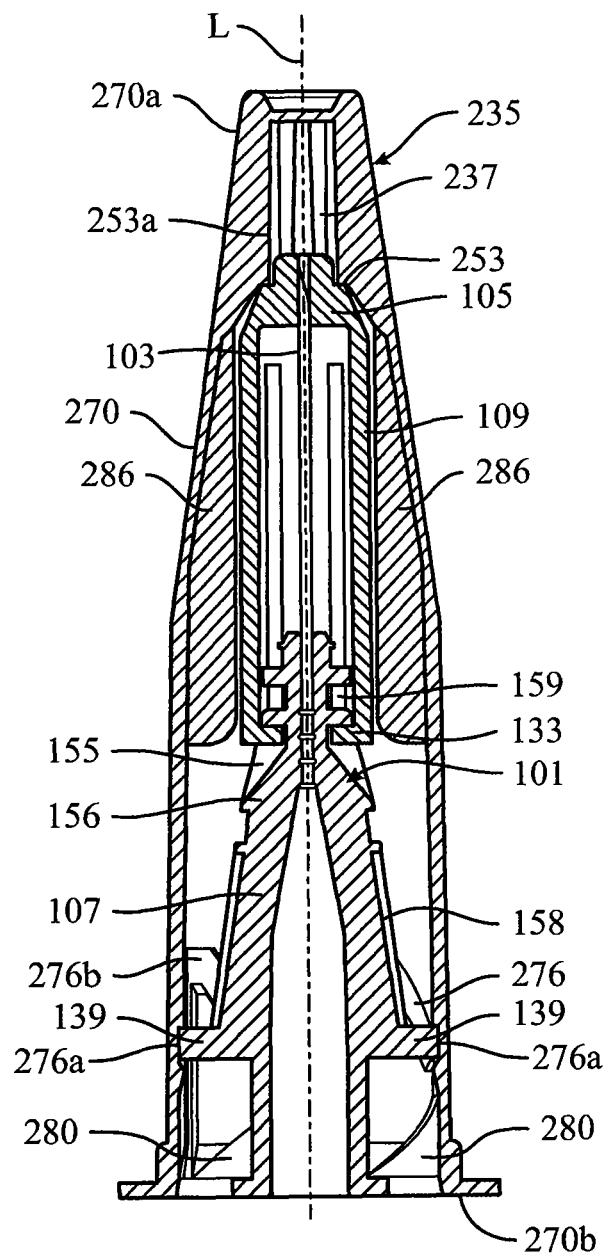
FIG. 19 is a center line cross section view of the safety needle and packing sleeve shown in FIG. 17 with the safety needle in an initial position.
Figure 20:
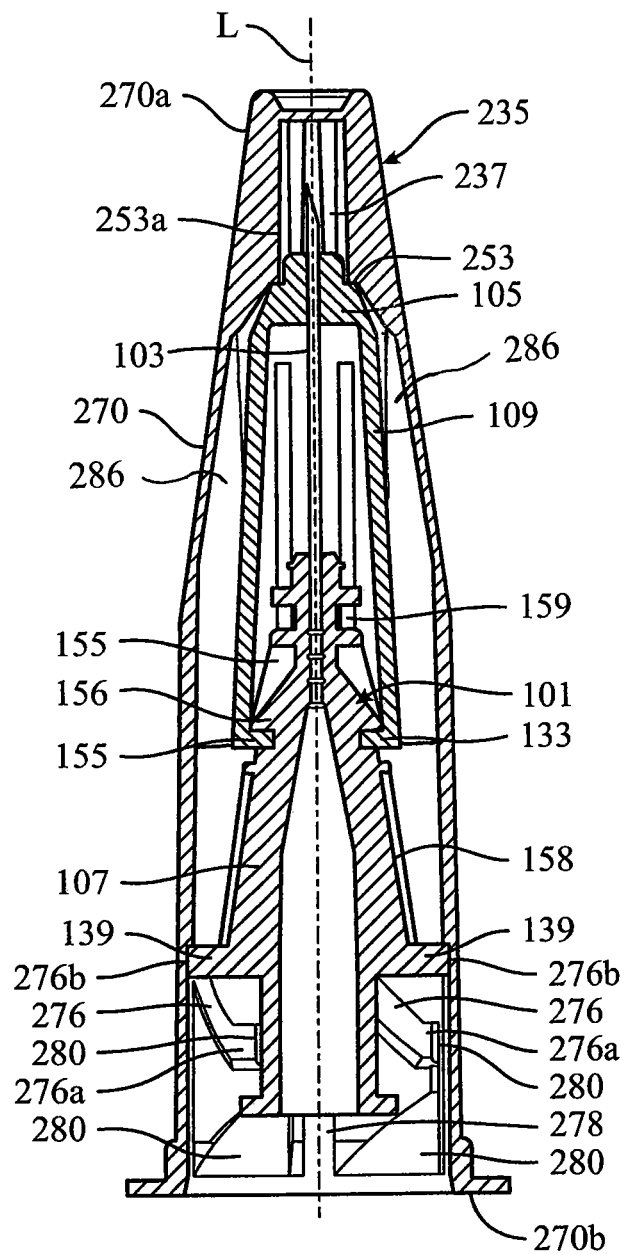
FIG. 20 is a center line cross section view of the safety needle and packing sleeve shown in FIG. 17 with the safety needle in an intermediate position.

Referring to FIGS. 19 and 20, the safety needle 101 is inserted into the body 270 in an initial position and is not removable from the body 270 in this position once assembled (FIG. 19). The retaining ribs 286 prevent the slidable sleeve 105 from unintentionally moving relative to the hub 107 and out of the initial position. For example, if the packing sleeve 235 is dropped on the proximal end 270b or is otherwise jolted, the slidable sleeve 105 is prevented from sliding toward the proximal end 270b of the body 270 because any deflection of the cantilever arms 109 is limited by the retaining ribs 286. As a result, the slidable sleeve 105 preferably cannot move until the cantilever arms 109 are twisted out of alignment with the retaining ribs 286. To remove the body 270 from the safety needle 101 or other injection or medical device, the user must twist the needle hub 207 relative to the body 270 with a predetermined amount of torque such that the projections 139 snap over the retaining bumps 280. The retaining bumps 280 also ensure that the safety needle 101 is fully secured to the syringe 42 because the projections 139 will not have the sufficient predetermined circumferential twisting force to overcome the retaining bumps 280 until the safety needle 101 is fully twisted onto the syringe 42. For example, if a user fails to fully tighten the safety needle 101 onto the syringe 42, when the user goes to remove the packing sleeve 235, the packing sleeve and safety needle 101 will twist together with respect to the syringe 42 until the threaded or luer connection between the safety needle 101 and the syringe 42 is fully engaged. Once the safety needle 101 can no longer be twisted relative to the syringe 42 the user will continue twisting the packing sleeve 235 until the twisting force surpasses the predetermined amount of torque such that the projections 139 snap or slide over the retaining bumps 280 and the packing sleeve 235 twists relative to the safety needle 101 and syringe 42. Though it is preferred that the retaining bumps 280 extend generally parallel to the longitudinal axis L of the body 270, the retaining bumps 280 may be positioned generally perpendicular to the longitudinal axis L or at an angle to the longitudinal axis L so that the initial movement of the needle hub 107 with respect to the body 270 is at least partially toward the distal end 270a of the body 270.

After the initial twist, or other movement to overcome the retaining bumps 280, the user then urges the needle hub 107, or whatever the needle hub 107 may be connected to, toward the distal end 270a of the body 270. Pushing the needle hub 107 toward the distal end 270a of the body 270 causes the projections 139 to follow the paths of the activation legs 276 such that the needle hub 107 twists and the needle hub 107 advances toward the distal end 270a. Twisting of the needle hub 107 also twists the slidable sleeve such that the cantilever arms 109 are unaligned with the retaining ribs 286 and therefore enabling the cantilever arms 109 to move in the radial direction as the slidable sleeve slides over the needle hub 107. Similar to an above described embodiment, urging the needle hub 107 toward the distal end 270a causes the needle hub 107 to slide up into the cantilever arms 109 of the slideable sleeve 105 and into the activated or intermediate position (FIG. 20). In order to remove the body 270 from the safety needle 101, the projections 139 must first follow the path set forth by the activation legs 276. The activation legs 276 terminate at a second end 276b at which point the safety needle 101 is in the activated or intermediate position. The releasing legs 278 extend in a direction that is generally parallel with the longitudinal axis L of the body 270 from the second ends 276b such that once the projections 139 reach the second ends 276b and the safety needle 101 is in the intermediate position, the projections 139 may be pulled along the releasing legs 278 and out of the body 270. The tracks 274 prevents the user from having to remember to push the safety needle 101 toward the distal end 270a of the body 270 to set the safety needle 101 in the intermediate position before removing the body 270 because the body 270 cannot be removed from the safety needle 101 until the safety needle 101 is set in the intermediate position.

Referring to FIG. 21-25J, there is shown another preferred embodiment of the safety needle, generally designated 301. The safety needle 301 is similar to the previously described embodiments and similar numbering has been used to indicate similar elements. The safety needle 301 differs from the other embodiments as set forth below. The safety needle is for automatically covering a tip 303a (FIG. 25E) of a needle 303 following removal of the needle 303 from the epidermis 48 and subcutaneous tissue 49, generally referred to as skin 48 of a patient (not otherwise shown).

Figure 21:
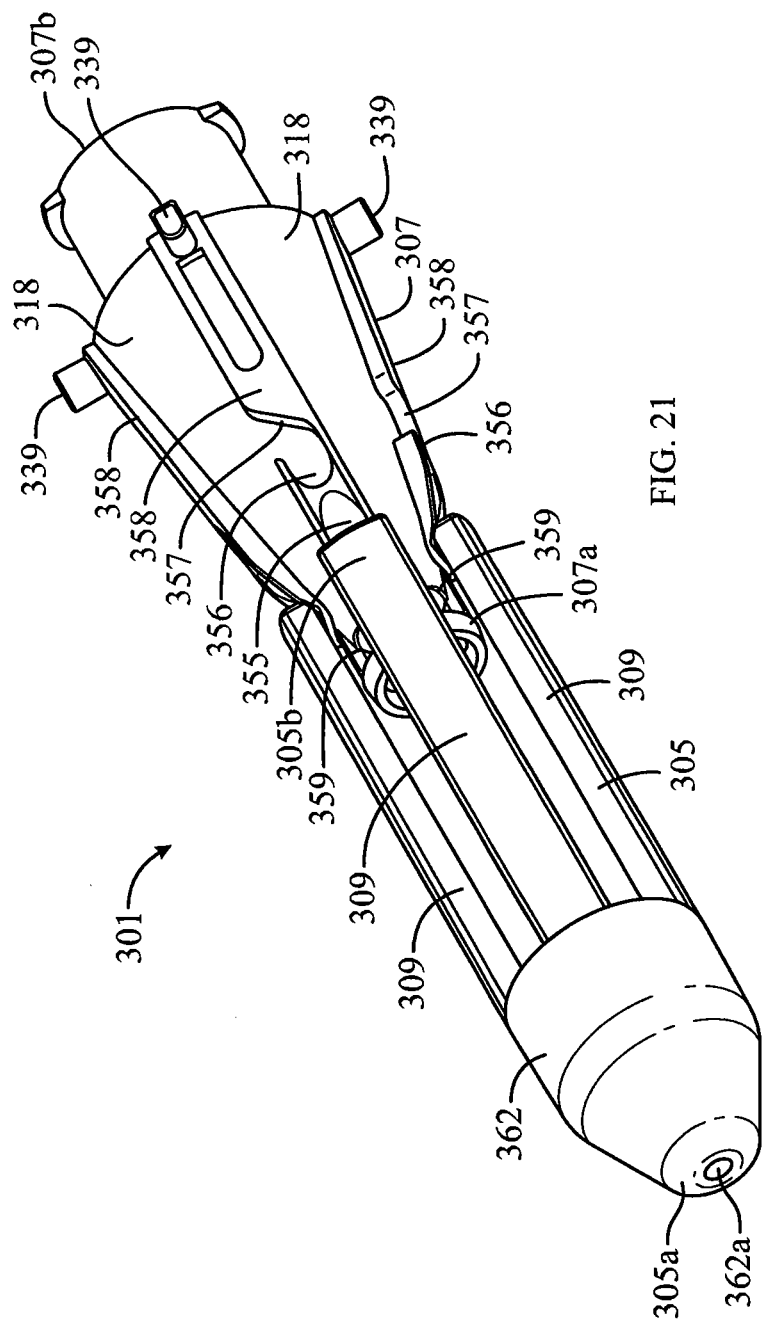
FIG. 21 is a perspective view of a safety needle in accordance with another embodiment of the present invention in an initial position.

Referring, to FIG. 21, the hollow needle 303 has a longitudinal axis (not shown) that extends along the length of the needle 303. A needle hub (hub) 307 is mounted onto a portion of the needle 303 and has an outer surface 318, a receiving end 307b distal to the tip 303a of the needle 303 and an injection end 307a proximal to the tip 303a of the needle 303. The hub 307 is preferably co-molded or affixed to the needle 303 with an epoxy or other fastening device or substance such that the safety needle 301 can be mounted to a needless syringe 2 (FIG. 1). However, the safety needle 301 may be mounted over a needle that is already affixed to the syringe (not shown) during use. The injection end 307a of the hub 307 preferably includes at least one and preferably four equally spaced recesses 359 extending radially inwardly. The recesses 359 may also be a circumferential slot 159 as described above. At least a portion of the outer surface 318 of the hub 307 tapers inwardly toward the injection end 307a. The hub 307 is preferably at least partially frusto-conical in shape such that the outer surface 318 has a straight line taper, but the outer surface 318 may be concavely tapered or tapered in some other manner.

The hub 307 preferably includes at least one and preferably four ramped indents 355. The hub 307 also preferably includes at least one and preferably four catches 356 spaced axially from the ramped indents 355. Each catch 356 preferably includes a cammed surface 357 axially extending from the catch 356. Axially extending guides 358 preferably extend from the cammed surfaces 357. The cammed surface 357 and guides 358 form a helical track as described further below.

Figure 23:
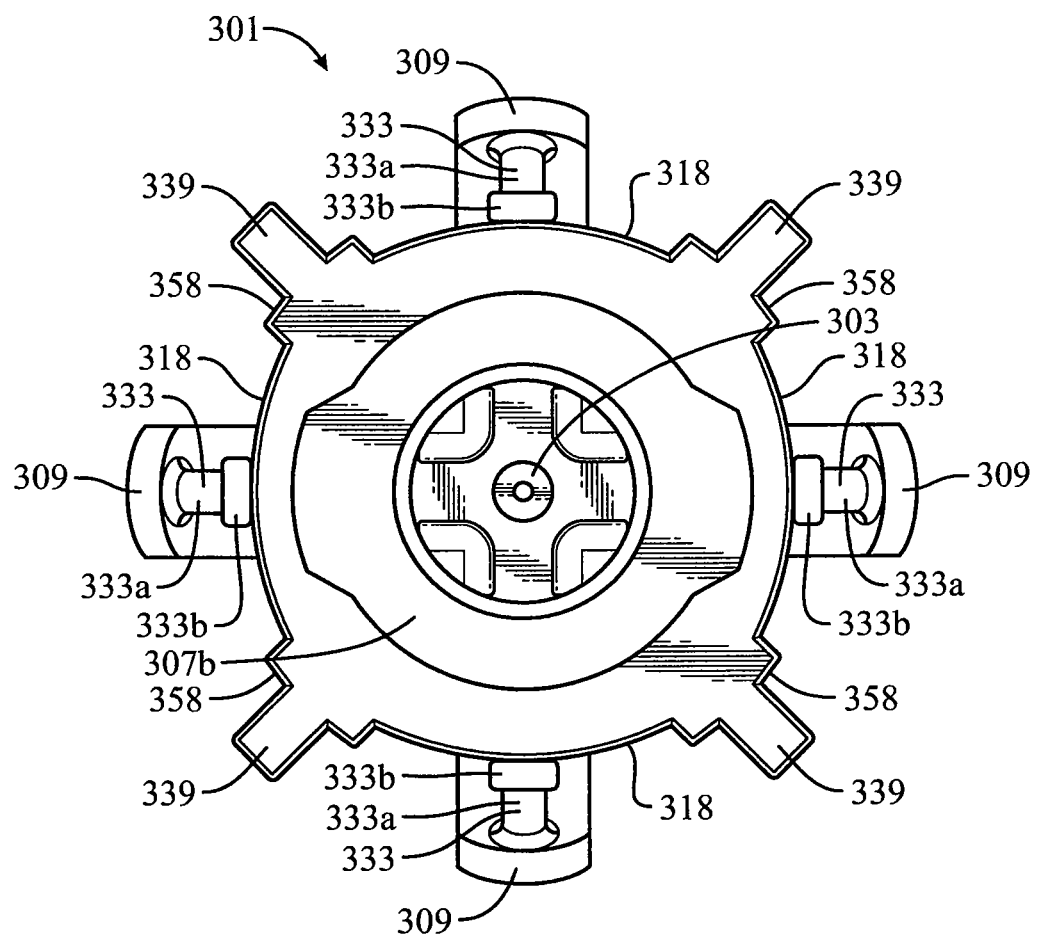
FIG. 23 is a rear elevational view of the proximal end of the safety needle shown in FIG. 21 with the slidable sleeve in a retracted position.

Referring to FIG. 23, the outer surface 318 of the hub 307 decreases in radial dimension from the needle 303 moving circumferentially from each catch 356 such that the outer surface 318 is partially flattened between each catch 356. The outer surface 318 is preferably convex in the circumferential direction and has a radius of curvature that is larger than the distance from the needle 303 to the outer surface 318 but the outer surface 318 may have any shape such an concave. The outer surface 318 of the hub 307 is preferably convexly and smoothly shaped to ensure smooth operation as described further below.

Figure 22:
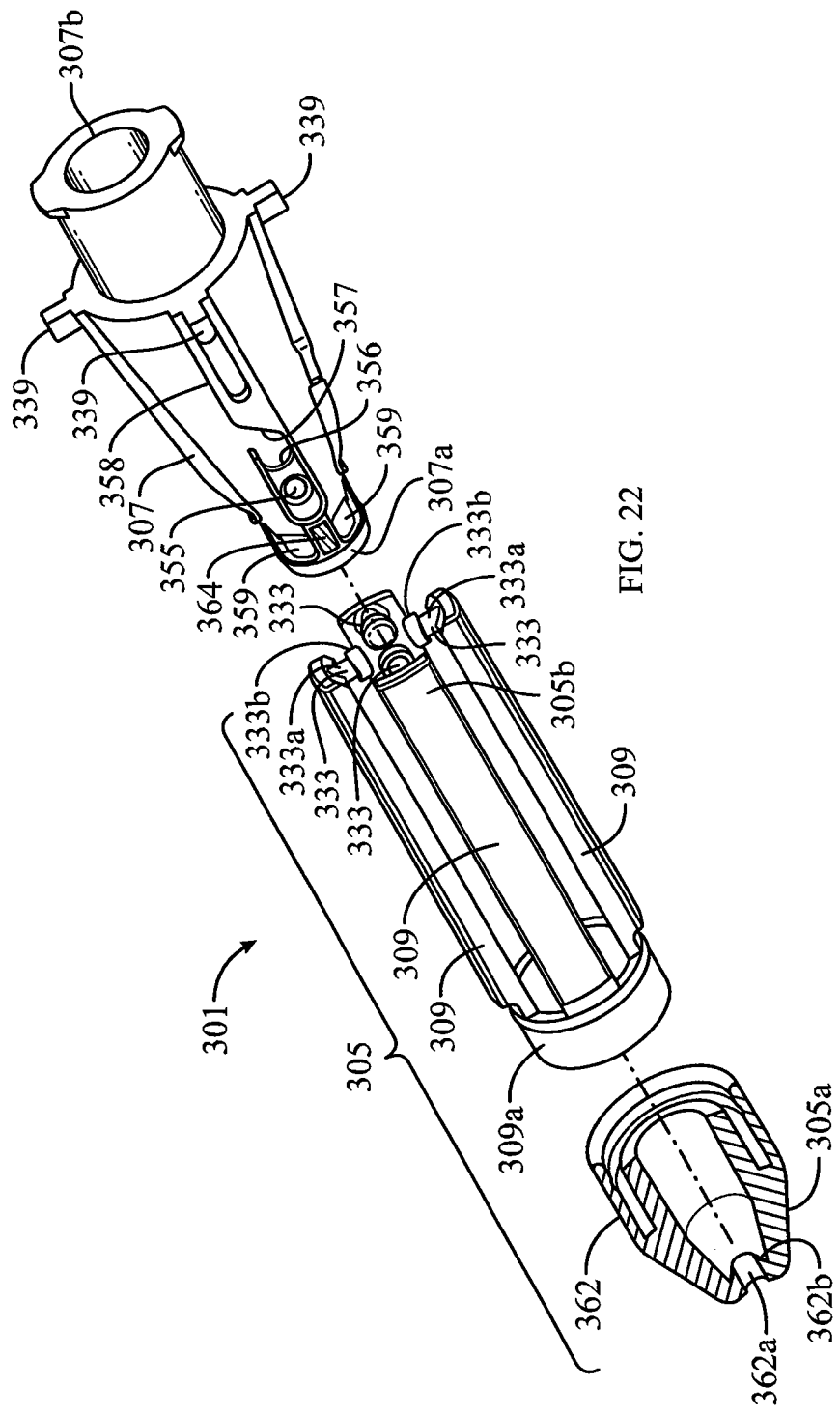
FIG. 22 is an exploded perspective view of the safety needle shown in FIG. 21 with the nose cone shown in cross section.
Figure 24:
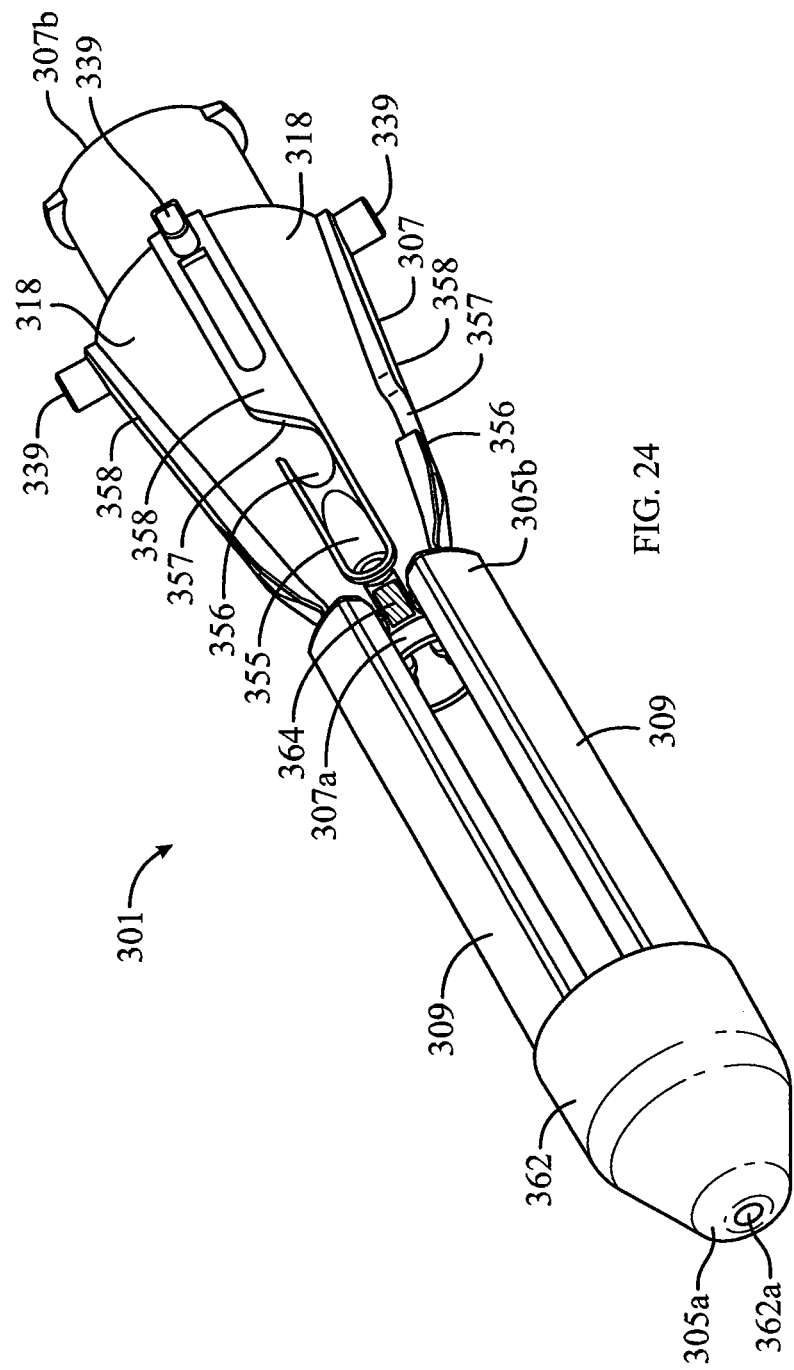
FIG. 24 is a perspective view of the safety needle shown in FIG. 21 in an extended position.

Referring to FIGS. 22 and 24, the hub 307 includes at least one and preferably four circumferentially spaced indicator markings 364. The indicator markings 364 are visual marks that are preferably circumferentially inline with the ramped indents 355 and are between each of recesses 359 or at least between the ramped indents 355 and the injection end 307a of the hub 307. The indicator markings 364 are preferably a green colored sticker that is affixed to the hub 307 by an epoxy but the indicator markings 364 may be any marking that is visually distinguishable from the hub 307 such as a textured surface, paint, a light, a reflector or co-molded material.

Referring to FIGS. 21 and 22, a slidable sleeve 305 is slidably mounted to the hub 307. The slidable sleeve 305 has a mounting end 305b distal to the tip 303a of the needle 303 and an injection end 305a proximal to the tip 303a of the needle 303. The slidable sleeve 305 preferably includes a nose cone 362 and at least one and preferably four resilient cantilever arms 309. The cantilever arms 309 extend in the axial direction and have a resilient flexure in the radial direction. The cantilever arms 309 are preferably equally spaced circumferentially from each other but may be asymmetrically spaced or joined together such that the slidable sleeve 305 forms an enclosed sheath. The cantilever arms 309 are preferably joined by a ring 309a that is then mounted into the nose cone 362. However, the cantilever arms 309 may be integrally formed with the nose cone 362 without the need for the ring 309a. The nose cone 362 has a needle hole 362a. The material surrounding the needle hole 362a preferably extends axially into the nose cone 362 such that an axially extending dip 362b is formed around the needle hole 362a inside of the nose cone 362. Each cantilever arm 309 preferably includes a projection or foot 333 extending radially inwardly proximate the mounting end 305a of the slidable sleeve 305. Each foot 333 preferably has an enlarged end such that each foot 333 has an enlarged distal width 333b and a reduced proximal width 333a (see FIGS. 22 and 23). Each foot 333 is in sliding contact with the outer surface 318 of the hub 307 during use.

The tip 303a of the needle 333 is located inside of the slidable sleeve 305 in an extended position (FIG. 24) and the tip 303a of the needle 303 projects from the slidable sleeve 305 in a retracted position (FIGS. 25F and 25G). The feet 333 are mounted within the corresponding ramped indents 355 in an initial position (FIG. 21). The initial position is preferably axially between the retracted and the extended positions but the extended position may be between the initial position and the retracted position such that the slidable sleeve is held more securely in the extended position. The outer surface 318 of the hub 307 deflects the feet 333, and correspondingly, the slidable sleeve 305, outwardly in a radial direction as the slidable sleeve 305 slides axially toward the receiving end 307b of the hub 307.

Figures 25A, 25B, 25C, 25D:
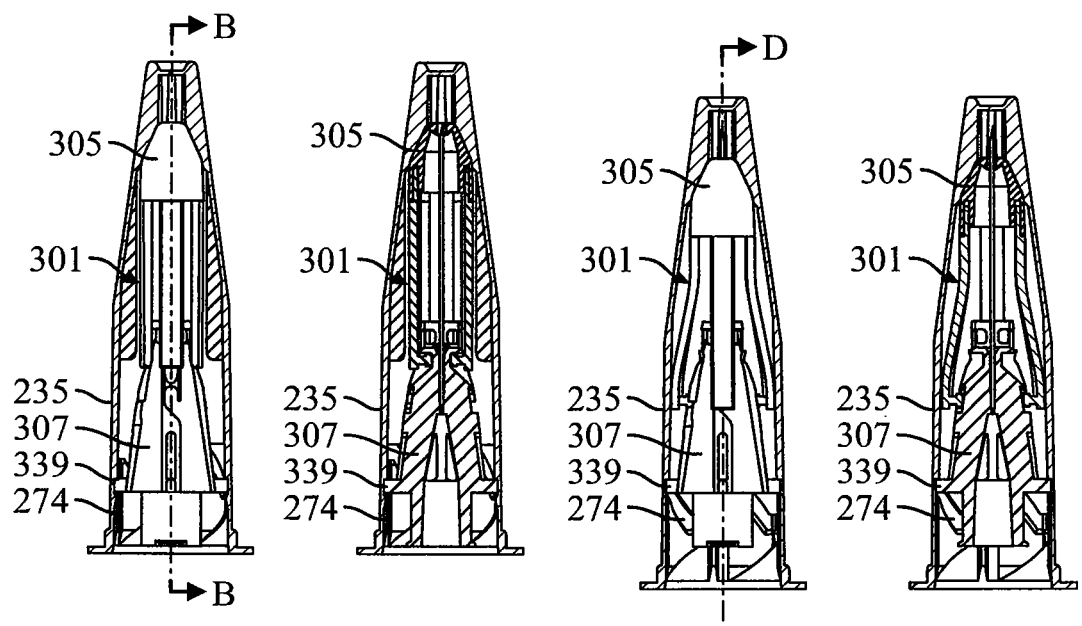
FIG. 25A is a side elevational view of the safety needle shown in FIG. 21 in the initial position with the packing sleeve shown in FIG. 17 in cross section.
FIG. 25B is a cross sectional view of the safety needle and packing sleeve shown in FIG. 25A taken along line B-B.
FIG. 25C is a side partial cross sectional view of the safety needle and packing sleeve shown in FIG. 25A in an intermediate position.
FIG. 25D is a cross sectional view of the safety needle and packing sleeve shown in FIG. 25C taken along line D-D.
Figure 25E:
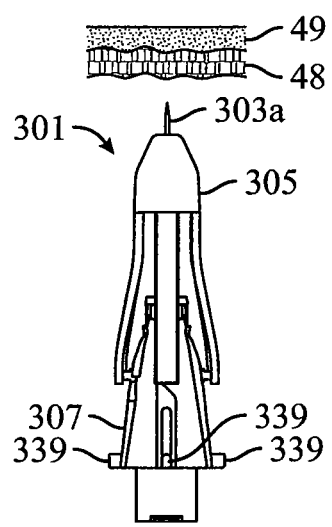
FIG. 25E is a side elevational view of the safety needle shown in FIG. 25A after removing the packing sleeve and in the intermediate position just prior to injection.

Referring to FIGS. 25A-25J, the safety needle 301 is preferably initially sealed within the packing sleeve 235 described above (FIGS. 25A-25D). The packing sleeve 235 must be first moved further over the hub 307 before the packing sleeve 235 can be removed from the safety needle 301 (FIGS. 25C-25D). Removing the packing sleeve 235 urges the slidable sleeve 305 over the hub 307 such that the feet 333 are urged along the ramped indents 355 and into the catches 356. The catches 356 retain the slidable sleeve 305 in an intermediate position (FIG. 25E). The tip 303a of the needle 303 preferably extends slightly from the slidable sleeve 305 in the intermediate position though the tip 303a may be partially shrouded or entirely covered. The slidable sleeve 305 is preferably spring biased against the hub 307 in the intermediate position. The tip 303a of the needle 303 is then injected into the skin 48 (FIGS. 25F and 25G). The needle 303 may extend into the skin 48 and into the subcutaneous tissue 49 depending on the type of injection. The needle 303 may have a predetermined maximum exposed length to prevent over insertion into the skin 48. As the needle 303 extends into the skin 48 the skin 48 abuts against the injection end 305a of the slidable sleeve 305 generating a displacement force in the axial direction. The displacement force urges the slidable sleeve 305 axially with respect to the hub 307 such that the feet 333 contact the cammed surfaces 357 and twist the slidable sleeve with respect to the hub 307. The decrease of the radial dimension of the hub 307 causes the feet 333 to twist further away from the catches 356 such that the feet 333 are preferably spaced between the catches 356 (see FIGS. 23, 25F and 25G). The radially outwardly extending guides 358 prevent the slidable sleeve 305 from twisting too far in either circumferential direction if an external force twists the slidable sleeve 305 relative to the hub 307. However, the cammed surfaces 357 and the guides 358 may be omitted such that the direction of the feet 333 is dictated only by the slope of the outer surface 318 of the hub 307. Alternatively, the guides 358 may be more narrowly positioned to form a helical track that the feet 333 more closely follow. As the feet 333 slide toward the retracted position, a restoring force is generated within the slidable sleeve due to the radial expansion of the cantilever arms 309. Once the feet 333 are circumferentially spaced from the catches 356 the restoring force urges the slidable sleeve to move toward the injection end 307a of the needle hub 307 down the outer surface 318 of the hub 307 and into the extended position upon removal of the displacement force (i.e. withdraw of the needle 303 from the skin 48). The feet 333 then slide into and are retained within the respective recess 359 in the extended position to "lock" the slidable sleeve 305 over the tip 303a of the needle 303 to prevent reuse and/or an accidental needle stick of the needle 303.

Referring to FIGS. 24, 25H and 25I, in the extended position, at least one of the indicator markings 364 is visible between at least two of the cantilever arms 309 to ensure to the user that the safety needle 301 is in the extended position and can be safely disposed of. The indicator marking 364 is preferably covered in the initial and intermediate positions. Alternatively, an additional indicator marking may be provided to indicate that the slidable sleeve 305 is in the intermediate position Such a configuration may be obtained by requiring a twist of the slidable sleeve 305 relative to the hub 307 between the initial and intermediate positions. Alternatively further, the indicator marking 364 may only be visible in the initial and intermediate positions and covered in the extended position to indicate that the safety needle 301 is not locked and ready for use.

Referring to FIGS. 25H-25J, once the safety needle 301 is in the extended position, urging the slidable sleeve 305 in a radial direction causes the needle hole 362a to unalign with the tip 303a of the needle 303 and dispose the tip 303a in the dip 362b. In this tilted position, the sharpened tip 303a may also extend into the polymeric material of the slidable sleeve 305 to further ensure that the needle 303 cannot be resused.

The slidable sleeve 305 preferably has little or no load in the initial position to reduce the cantilever arms from creeping. However, the slidable sleeve 305 may have a degree of biasing force on the hub 307 in the initial position. A resilient biasing ring (not shown) may be mounted over the mounting end 305b of the slidable sleeve 305 to add a biasing force or the recesses 359 may be positioned between the initial and intermediate positions. Alternatively, the ramped indents 355 may be recessed toward the needle 303 more than the recesses 359 such that the slidable sleeve 305 is initially not under any substantial load but the slidable sleeve 305 is biased against the hub 307 in the extended position. Additionally, the recesses 359 or the injection end 307a of the hub may extend varying radial lengths from the needle 303 or axially offset such that the slidable sleeve is automatically tilted in the extended position to prevent the tip 303a from aligning with the needle hole 362a.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A safety needle for automatically covering a tip of a needle following removal of the needle from a patient, the safety needle comprising:
    an injection device having an initial position and an intermediate position; and
    a packing sleeve having a generally hollow body surrounding at least a portion of the injection device in the initial position and the intermediate position, the body including at least one track having an activation leg and a releasing leg, the activation leg configured to slidingly engage with at least one member of the injection device to move the injection device to the intermediate position and wherein the packing sleeve is only removable from the injection device when the injection device is in the intermediate position.

2. The safety needle of claim 1, wherein the injection device has a needle with a tip, the needle extends from a hub, and a slidable sleeve at least partially surrounds the needle and is mounted on the hub, and wherein the at least one member extends radially from the hub.

3. The safety needle of claim 2, wherein the slidable sleeve abuts a ledge that at least partially forms a cavity at the distal end of the body and the needle extends into the cavity as the hub is moved toward the distal end of the body.

4. The safety needle of claim 2, the tip of the needle is at least partially shrouded by the slidable sleeve in the intermediate position.

5. The safety needle of claim 1, wherein pushing a proximal end of the injection device axially toward a distal end of the body advances the at least one member to a second end of the activation leg to set the injection device in the intermediate position and then subsequently pulling the proximal end of the injection device axially away from the packing sleeve releases the at least one member of the injection device from the packing sleeve with the injection device in the intermediate position.

6. The safety needle of claim 5, wherein the injection device must be first twisted relative to the packing sleeve before pulling the injection device axially away from a distal end of the packing sleeve.

7. The safety needle of claim 1, wherein the injection device further comprises:
    a hollow needle having a tip for injecting into the patient and a longitudinal axis;
    a hub mounted to the needle and having an outer surface, a receiving end distal to the tip of the needle and an injection end proximal to the tip of the needle, at least part of the outer surface of the hub tapering toward the injection end; and
    a slidable sleeve having a mounting end distal to the tip of the needle and an injection end proximal to the tip of the needle, the tip of the needle being located inside the slidable sleeve in an extended position, the tip of the needle projecting from the slidable sleeve in a retracted position, the slidable sleeve being slidably mounted to the hub between the receiving and injection ends of the hub in the initial position, the initial position being between the retracted and extended positions, the outer surface of the hub deflecting the slidable sleeve outwardly in a radial direction as the slidable sleeve slides axially toward the receiving end of the hub,
    wherein a displacement force urges the slidable sleeve from the initial position toward the retracted position generating a restoring force within the slidable sleeve, the restoring force urging the slidable sleeve to move toward the injection end of the needle hub and into the extended position upon removal of the displacement force.

8. The safety needle of claim 7, wherein the packing sleeve includes at least one retaining rib aligned with and preventing radial deflection of a portion of the slidable sleeve in the initial position and unaligned with and allowing radial deflection of the portion of the slidable sleeve in a position other than the initial position.

9. The safety needle of claim 1, wherein the at least one member can only be moved in a circumferential direction relative to the body out from a first end of the activation leg.

10. The safety needle of claim 1, wherein the at least one member is a radially extending projection.

11. The safety needle of claim 1, wherein a portion of the activation leg allows the injection device to rotate relative to the body.

12. The safety needle of claim 1, wherein a portion of the activation leg allows the at least one member to be advanced toward a distal end of the body.

13. A safety needle for automatically covering a tip of a needle following removal of the needle from a patient, the safety needle comprising:
    an injection device moveable between an initial position and an intermediate position, the injection device includes:
        a needle extending from a hub and having a tip, and
        a slidable sleeve at least partially surrounding the needle and mounted on the hub; and a packing sleeve having a generally hollow body surrounding at least a portion of the injection device in the initial position and the intermediate position, the generally hollow body including at least one track having an activation leg and a releasing leg, the at least one track configured to slidingly engage with at least one member of the injection device to move the injection device to the intermediate position and wherein the packing sleeve is only removable from the injection device when the injection device is in the intermediate position.

* * * * *